(12) United States Patent
Iseri et al.

(10) Patent No.: US 11,589,841 B2
(45) Date of Patent: Feb. 28, 2023

(54) ULTRASOUND IMAGING DEVICE, ULTRASOUND IMAGING SYSTEM, ULTRASOUND IMAGING METHOD AND ULTRASOUND IMAGING PROGRAM

(71) Applicant: FURUNO ELECTRIC CO., LTD., Nishinomiya (JP)

(72) Inventors: Kensuke Iseri, Sakai (JP); Satoshi Nakamura, Takatsuki (JP); Takuo Shimada, Kobe (JP); Tatsuo Arai, Takarazuka (JP)

(73) Assignee: FURUNO ELECTRIC CO., LTD., Nishinomiya (JP)

( * ) Notice: Subject to any disclaimer, the term of this patent is extended or adjusted under 35 U.S.C. 154(b) by 30 days.

(21) Appl. No.: 17/147,188

(22) Filed: Jan. 12, 2021

(65) Prior Publication Data

US 2021/0128117 A1   May 6, 2021

Related U.S. Application Data

(63) Continuation of application No. PCT/JP2019/024013, filed on Jun. 18, 2019.

(30) Foreign Application Priority Data

Jul. 13, 2018 (JP) .............................. JP2018-133151

(51) Int. Cl.
*A61B 8/14* (2006.01)
*A61B 8/08* (2006.01)
(Continued)

(52) U.S. Cl.
CPC .............. *A61B 8/5253* (2013.01); *A61B 8/14* (2013.01); *A61B 8/469* (2013.01); *A61B 8/5207* (2013.01);
(Continued)

(58) Field of Classification Search
CPC ......... A61B 8/5253; A61B 8/14; A61B 8/469; A61B 8/5207; A61B 8/463; A61B 8/0858;
(Continued)

(56) References Cited

U.S. PATENT DOCUMENTS 6,530,886 B1 * 3/2003 Ishida .................. A61B 8/0858
600/443
2009/0005683 A1   1/2009 Hashimoto et al.
(Continued)

FOREIGN PATENT DOCUMENTS

JP    2009-005755 A    1/2009
JP    2009-028096 A    2/2009
(Continued)

OTHER PUBLICATIONS

Moon et al., "Computer-Aided Diagnosis for the Classification of Breast Masses in Automated Whole Breast Ultrasound Images", Jan. 7, 2011, Ultrasound in Med. & Biol., vol. 37, No. 4, pp. 539-548 (Year: 2011).*
(Continued)

*Primary Examiner* — Patricia J Park
*Assistant Examiner* — Adil Partap S Virk
(74) *Attorney, Agent, or Firm* — Studebaker & Brackett PC

(57) ABSTRACT

The purpose is to provide an ultrasound imaging device capable of automatically detecting a boundary of a biological tissue in an ultrasound image. An ultrasound imaging device includes an image generation module which receives ultrasound waves transmitted from a surface of an analyte toward an inside of the analyte and reflected therein to generate an ultrasound image inside the analyte, a reference point setting module which sets a reference point of a tissue of interest of the ultrasound image, a first seed point impart- (Continued)

ing module which imparts one or more seed points to the ultrasound image with reference point, and a region demarcating module which demarcates a region to which the seed point belongs and divides an image region of the analyte included in the ultrasound image into a plurality of regions according to a type of tissue.

11 Claims, 14 Drawing Sheets

(51) Int. Cl.
  *G06T 7/11* (2017.01)
  *A61B 8/00* (2006.01)
  *G06T 7/00* (2017.01)
(52) U.S. Cl.
  CPC .............. *G06T 7/0014* (2013.01); *G06T 7/11* (2017.01); *A61B 8/463* (2013.01); *G06T 2207/10132* (2013.01); *G06T 2207/20021* (2013.01); *G06T 2207/20221* (2013.01); *G06T 2207/30092* (2013.01)
(58) Field of Classification Search
  CPC ..... A61B 8/462; A61B 8/4472; G06T 7/0014; G06T 7/11; G06T 2207/10132; G06T 2207/20021; G06T 2207/20221; G06T 2207/30092; G06T 2207/20156; G06T 7/0012; G06T 2207/20076; G06T 2207/30024; G06T 7/12; G01S 7/52065; G01S 7/52073
  See application file for complete search history.

(56) References Cited

U.S. PATENT DOCUMENTS

| | | | | |
|---|---|---|---|---|
| 2010/0068149 | A1* | 3/2010 | Zwijsen | A61P 3/00 424/9.5 |
| 2010/0161023 | A1* | 6/2010 | Cohen | A61B 17/1204 623/2.11 |
| 2010/0249589 | A1* | 9/2010 | Lysyansky | A61B 8/466 600/440 |
| 2011/0079082 | A1* | 4/2011 | Yoo | A61B 8/483 73/632 |
| 2013/0083982 | A1 | 4/2013 | Nakamura | |
| 2013/0322725 | A1* | 12/2013 | Enzmann | G06T 7/0012 382/132 |
| 2015/0005637 | A1* | 1/2015 | Stegman | A61B 8/5223 600/449 |
| 2015/0110373 | A1 | 4/2015 | Shaham et al. | |
| 2015/0238164 | A1* | 8/2015 | Cho | A61B 8/0858 600/443 |
| 2015/0359520 | A1* | 12/2015 | Shan | A61B 8/0858 600/443 |
| 2017/0221215 | A1* | 8/2017 | Shao | G06T 7/11 |
| 2018/0028137 | A1* | 2/2018 | Zhao | A61B 6/03 |
| 2018/0165808 | A1 | 6/2018 | Bagci et al. | |
| 2018/0199997 | A1* | 7/2018 | Pinto De Oliveira | A61B 6/461 |

FOREIGN PATENT DOCUMENTS

| | | |
|---|---|---|
| JP | 2013-075079 A | 4/2013 |
| JP | 2015-039521 A | 3/2015 |
| JP | 2018-068495 A | 5/2018 |

OTHER PUBLICATIONS

Xian et al., "Fully automatic segmentation of breast ultrasound images based on breast characteristics in space and frequency domains", Aug. 12, 2014, Pattern Recognition, pp. 485-497 (Year: 2014).*

Araujo, "Computer Aided Detection of Perforating Arteries in CT Angiography", Falculdaded de Engenharia Universidade do Porto, Jun. 2016 (Year: 2014).*

Ikezoe et al. Part 1 of this series: "Quantitative and qualitative evaluation of skeletal muscle using ultrasound imaging equipment," Physical Therapy vol. 42, No. 1 65, p. 71 (2015).

Juan Shan et al.; "A novel automatic seed point selection algorithm for breast ultrasound images"; 2008 19th International Conference on Pattern Recognition; Dec. 8-11, 2008; pp. 1-4; Tampa FL, IEEE.

Melouah Ahlem et al.; "Overview of Automatic Seed Selection Methods for Biomedical Images Segmentation"; The International Arab Journal of Information Technology; May 2018; pp. 499-504; vol. 15; No. 3.

The extended European search report issued by the European Patent Office dated Mar. 23, 2022, which corresponds to European Patent Application No. 19834870.8-1210 and is related to U.S. Appl. No. 17/147,188.

An Office Action mailed by the Indian Patent Office dated Jun. 30, 2022, which corresponds to Indian Patent Application 202127006115 and is related to U.S. Appl. No. 17/147,188.

* cited by examiner

ULTRASOUND IMAGING DEVICE, ULTRASOUND IMAGING SYSTEM, ULTRASOUND IMAGING METHOD AND ULTRASOUND IMAGING PROGRAM

CROSS-REFERENCE TO RELATED APPLICATION(S)

This application is a continuation of PCT International Application No. PCT/JP2019/024013, which was filed on Jun. 18, 2019, and which claims priority to Japanese Patent Application Ser. No. 2018-133151 filed on Jul. 13, 2018, the entire disclosures of each of which are herein incorporated by reference for all purposes.

TECHNICAL FIELD

The present invention relates to an ultrasound imaging device, an ultrasound imaging system, an ultrasound imaging method and an ultrasound imaging program for imaging the inside of a subject by ultrasound waves.

BACKGROUND

Conventionally, in order to acquire a tomographic image of a living body, a CT (Computed Tomography) device or an MRI (Magnetic Resonance Imaging) device has been used. Since these devices are large and expensive, and there is a problem of exposure to radiation, a technique for obtaining tomographic images using ultrasound waves has been developed in recent years. For example, Non-Patent Document 1 discloses a technique for evaluating muscle mass and muscle quality in an ultrasound tomographic image on the basis of a boundary between a muscle and another tissue such as subcutaneous fat or a boundary between muscles.

REFERENCE DOCUMENTS OF CONVENTIONAL ART

[Non-Patent Document 1]
Yoshihiro Fukumoto, 3 others, "Quantitative and qualitative evaluation of skeletal muscle using ultrasound diagnostic imaging equipment" Physical Therapy, Japanese Society of Physical Therapists, 2015, Vol. 42, No. 1, p. 65-71

At present, in order to detect the boundary of a biological tissue in an ultrasound tomographic image, seed points having different attributes (color, etc.) are manually imparted according to the type of the tissue, and a region according to the type of the tissue is extracted. However, this method has a problem that the work of imparting seed points is complicated and the burden on the user is large. In addition, when the user is a non-medical worker who is not familiar with the structure of the biological tissue, it is difficult to accurately impart the seed point.

SUMMARY

An object of the present invention is to provide an ultrasound imaging device capable of automatically detecting a boundary of a biological tissue in an ultrasound image.

An ultrasound imaging device includes an image generation module which receives ultrasound waves transmitted from a surface of an analyte toward an inside of the analyte and reflected therein to generate an ultrasound image of the inside of the analyte, a reference point setting module which sets a reference point of a tissue of interest of the ultrasound image, a first seed point imparting module which imparts one or more seed points to the ultrasound image with reference to the reference point, and a region demarcation module which demarcates a region to which the seed point belongs and divides an image region of the analyte included in the ultrasound image into a plurality of regions according to the type of tissue.

An ultrasound imaging system includes a probe for transmitting ultrasound waves from a plurality of mutually different positions on a surface of an analyte toward the inside of the analyte and receiving the ultrasound waves reflected in the inside of the analyte, and an ultrasound imaging device according to the present invention.

An ultrasound imaging method includes an image generation step of receiving ultrasound waves transmitted from a surface of an analyte toward an inside of the analyte and reflected therein to generate an ultrasound image of the inside of the analyte; a reference point setting step of setting a reference point of a tissue of interest of the ultrasound image; a seed point imparting step of imparting one or more seed points to the ultrasound image with the reference point as a reference; and a region demarcation step of demarcating a region to which the seed point belongs and dividing an image region of the analyte included in the ultrasound image into a plurality of regions according to a type of the tissue.

An ultrasound imaging program wherein a computer is operated as an image generation module which receives ultrasound waves transmitted from a surface of an analyte toward an inside of the analyte and reflected therein to generate an ultrasound image inside the analyte, a reference point setting module which sets a reference point of a tissue of interest in the ultrasound image, a first seed point imparting module which imparts one or more seed points to the ultrasound image with reference to the reference point, and a region demarcation module which demarcates a region to which the seed point belongs, and divides an image region of the analyte included in the ultrasound image into a plurality of regions according to a type of the tissue.

According to the present invention, the boundary of the biological tissue can be automatically detected in the ultrasound image.

BRIEF DESCRIPTION OF DRAWINGS

The summary above, as well as the following detailed description of illustrative embodiments, is better understood when read in conjunction with the appended drawings. For the purpose of illustrating the present disclosure, exemplary constructions of the disclosure are shown in the drawings. However, the present disclosure is not limited to specific methods and instrumentalities disclosed herein. Moreover, those in the art will understand that the drawings are not to scale. Wherever possible, like elements have been indicated by identical numbers.

DETAILED DESCRIPTION

Figure 1:
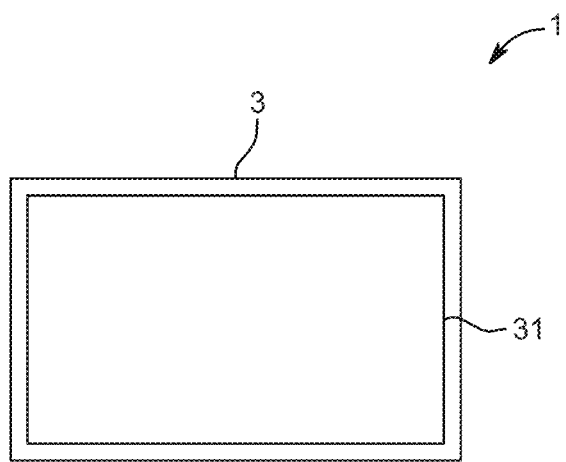
FIG. 1 is a schematic diagram showing a configuration of an ultrasound imaging system according to a first embodiment.
Figure 1:
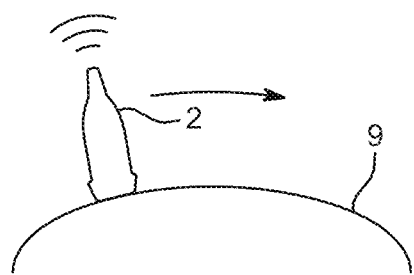

Embodiments of the present invention will now be described in detail with reference to the accompanying drawings. In the following description and the drawings, the same reference numerals indicate the same or similar components, and therefore redundant description of the same or similar components is omitted.

FIG. 1 is a schematic diagram showing a configuration of an ultrasound imaging system 1 according to a first embodiment. The ultrasound imaging system 1 includes a probe 2 and an ultrasound imaging device 3.

The probe 2 is a device for transmitting ultrasound waves from a plurality of mutually different positions on the surface of the analyte 9 toward the inside of the analyte 9 and receiving the ultrasound waves reflected in the inside of the analyte 9, and in this embodiment, the device can grasp and move. An ultrasound transmission/reception surface in which a plurality of ultrasound transducers is arranged in a row is provided at the lower end of the probe 2. When obtaining a tomographic image (or a cross-sectional image) of the analyte 9, the subject makes the ultrasound transmission/reception surface of the probe 2 abut on the analyte 9 and moves the probe 2 along the surface of the analyte 9 (scan by the probe 2). During this time, the probe 2 intermittently transmits ultrasound waves from the ultrasound transmission/reception surface toward the inside of the analyte 9, and receives the ultrasound waves reflected in the inside of the analyte 9 on the ultrasound transmission/reception surface. Thus, the probe 2 outputs an electric signal (echo signal) indicating the received ultrasound wave.

The probe 2 operates in a linear scan mode for acquiring a linear scan image, but may operate in a sector scan mode for acquiring a sector scan image, may operate in both a linear scan mode and a sector scan mode, or may operate in other modes or in combination with other modes. Further, in the present embodiment, the analyte 9 is mainly the abdomen, but the biological portion included in the analyte 9 is not particularly limited.

The ultrasound imaging device 3 is connected to the probe 2 by radio such as WiFi (registered trademark). In the present embodiment, the ultrasound imaging device 3 is constituted by, for example, a tablet terminal, and has a function of generating a plurality of ultrasound images based on echo signals received from the probe 2, and displaying an ultrasound stitched image obtained by stitching the ultrasound images.

The ultrasound imaging device 3 is not particularly limited as long as it can display an image, and can be configured by a general-purpose personal computer, a smart phone, or the like. The connection method between the probe 2 and the ultrasound imaging device 3 is not particularly limited, and may be a wired connection.

Figure 2:
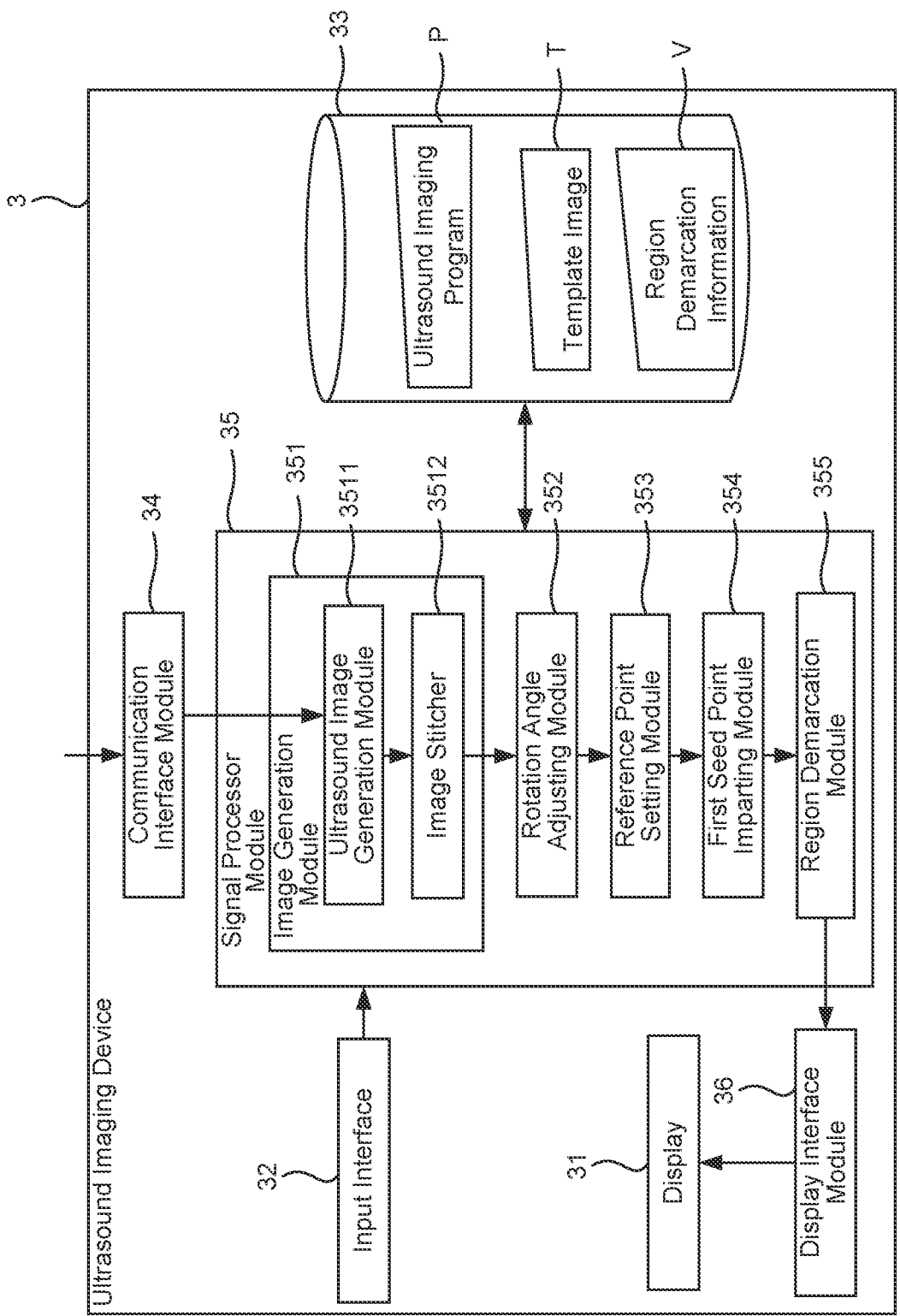
FIG. 2 is a block diagram showing a configuration of an ultrasound imaging device according to a first embodiment.

FIG. 2 is a block diagram showing the configuration of the ultrasound imaging device 3. The ultrasound imaging device 3 includes, as a hardware configuration, a display 31, an input interface 32, an auxiliary storage 33, a communication interface module (I/F module) 34, and a display interface module (I/F module) 36.

The display 31 may be, for example, a liquid crystal display, a plasma display, an organic EL display, or the like. Note that the display 31 may be constructed as a separate device from the ultrasound imaging device 3.

The input interface 32 is, for example, a touch panel provided on the surface of the display 31. Through the input interface 32, the subject can perform an input operation on the image displayed on the display 31.

The auxiliary storage 33 is a nonvolatile storage device for storing an operating system (OS), various control programs, and data generated by the programs, and is constituted by, for example, embedded Multi Media Card (eMMC) or Solid State Drive (SSD). The auxiliary storage 33 stores an ultrasound imaging program P, a template image T and region demarcation information V. The ultrasound imaging program P may be installed in the ultrasound imaging device 3 via a network such as the Internet. Alternatively, the ultrasound imaging program P may be installed in the ultrasound imaging device 3 by causing the ultrasound imaging device 3 to read a computer-readable non-temporary tangible recording medium such as an SD card on which the ultrasound imaging program P is recorded. The template image T and the region demarcation information V will be described later.

The communication interface module 34 transmits and receives data to and from an external device, and in this embodiment, demodulates a signal received from the probe 2 and modulates a control signal for transmission to the probe 2.

The display interface module 36 displays various image data generated by the arithmetic processing of the ultrasound imaging device 3 on the display 31 by developing the image data in the VRAM, and displays, for example, an ultrasound stitched image generated by a signal processor module 35 (also referred as "processing circuitry", described later) described later on the display 31.

Although not shown, the ultrasound imaging device 3 further includes, as other hardware configurations, a processor such as a CPU for performing data processing, and a memory (main storage) used by the processor in a work area for data processing.

The ultrasound imaging device 3 has the signal processor module 35 as a software configuration. The signal processing module (or "processing circuitry") 35 is a functional block realized by the processor executing the ultrasound imaging program P, and has a function of processing the echo signal received from the probe 2 to generate an ultrasound stitched image of the analyte 9, dividing the image region of the analyte 9 into a plurality of regions according to the type of tissue, and displaying each region on the display 31 in a distinguishable manner. To realize this function, the signal processor module 35 includes an image generation module 351, a rotation angle adjusting module 352, a reference point setting module 353, a first seed point imparting module 354, and a region demarcation module 355. The signal processor module (or "processing circuitry") 35 may be implemented in hardware by a logic circuit formed on an integrated circuit.

The image generation module 351 is a functional block for generating an ultrasound image inside the analyte 9 from the echo signal received from the probe 2, and includes an ultrasound image generation module 3511 and an image stitcher 3512.

The ultrasound image generation module 3511 receives ultrasound waves transmitted from a plurality of mutually different positions on the surface of the analyte 9 toward the inside of the analyte 9 and reflected inside, and generates ultrasound images corresponding to the respective positions. The probe 2 transmits ultrasound waves toward the inside of the analyte 9 from a plurality of mutually different positions on the surface of the analyte 9 according to a control signal transmitted from the ultrasound imaging device 3 while moving the surface of the analyte 9, receives the ultrasound waves reflected inside the analyte 9, and outputs an echo signal to the ultrasound imaging device 3. Thus, each time the probe 2 receives the ultrasound wave, an echo signal is inputted to the ultrasound image generation module 3511, and the ultrasound image generation module 3511 generates an ultrasound image corresponding to a plurality of mutually different positions on the surface of the analyte 9 from the echo signal. Although the number of generated ultrasound images varies depending on the transmission/reception time of the ultrasound waves by the probe 2 and the period of transmission/reception, it is assumed that n (n is a positive integer) ultrasound images are generated in this embodiment.

The function of the ultrasound image generation module 3511 may be provided in a control device for controlling the probe 2. In this case, the controller may be connected to the ultrasound imaging device 3, or the controller may store the ultrasound image and transmit the ultrasound image to the ultrasound imaging device 3 via a recording medium.

The image stitcher 3512 is a functional block that stitches the ultrasound image generated by the ultrasound image generation module 3511 at each position on the surface of the analyte 9 to generate an ultrasound stitched image of the cross section of the analyte 9. Well-known techniques can be applied to the stitching of ultrasound images, and in this embodiment, for example, the ultrasound images are stitched using feature point matching between the ultrasound images. In the present embodiment, the term "cross section" is a concept including not only a circular cross section but also a partial cross section.

In this method, feature points are detected from the first ultrasound image and the second ultrasound image. Then, the feature points of the first ultrasound image and the second ultrasound image are matched to calculate the homogeneous transformation matrix of the first ultrasound image and the second ultrasound image. Specifically, when the second ultrasound image is rotated clockwise by θ with respect to the first ultrasound image, and translated by $t_x$ in the x-axis direction and by $t_y$ in the y-axis direction, and the feature points of the first ultrasound image and the second ultrasound image coincide, homogeneous transformation matrix R to move the coordinate system of the second ultrasound image so as to be aligned with the first ultrasound image is as follows:

$$R = \begin{bmatrix} \cos\theta & -\sin\theta & t_x \\ \sin\theta & \cos\theta & t_y \\ 0 & 0 & 1 \end{bmatrix}$$

That is, when the feature point (x, y) on the first ultrasound image moves to the feature point (x', y') on the second ultrasound image, the relation is as follows:

$$\begin{bmatrix} x' \\ y' \\ 1 \end{bmatrix} = R \begin{bmatrix} x \\ y \\ 1 \end{bmatrix}$$

Since errors are included in the coordinates of the feature points and errors are included in the correspondence relationship itself determined by the influence of noise, outliers adversely affecting calculation are excluded by the Random Sample Consensus (RANSAC) algorithm. A nonlinear least squares method such as the Gauss-Newton method and the Levenberg Markert method can be used for calculating the positional relationship.

The calculation of the homogeneous transformation matrix R is sequentially performed on two ultrasound images in the generation order adjacent to each other up to the (n−1)-th ultrasound image and the nth ultrasound image. Assuming that the homogeneous transformation matrix from the (k+1)-th (1≤k≤n−1) ultrasound image to the k-th ultrasound image is $R_k$, the homogeneous transformation matrix from the (k+1)-th ultrasound image to the first ultrasound image is $R_1 R_2 \ldots R_k$. The coordinate system of the first ultrasound image is called the world coordinate system, and the coordinates of all the ultrasound images can be calculated by calculating a homogeneous transformation matrix to the world coordinate system for all the ultrasound images. Then, a single ultrasound stitched image is generated by blending the pixels of all the ultrasound images.

Figure 3:
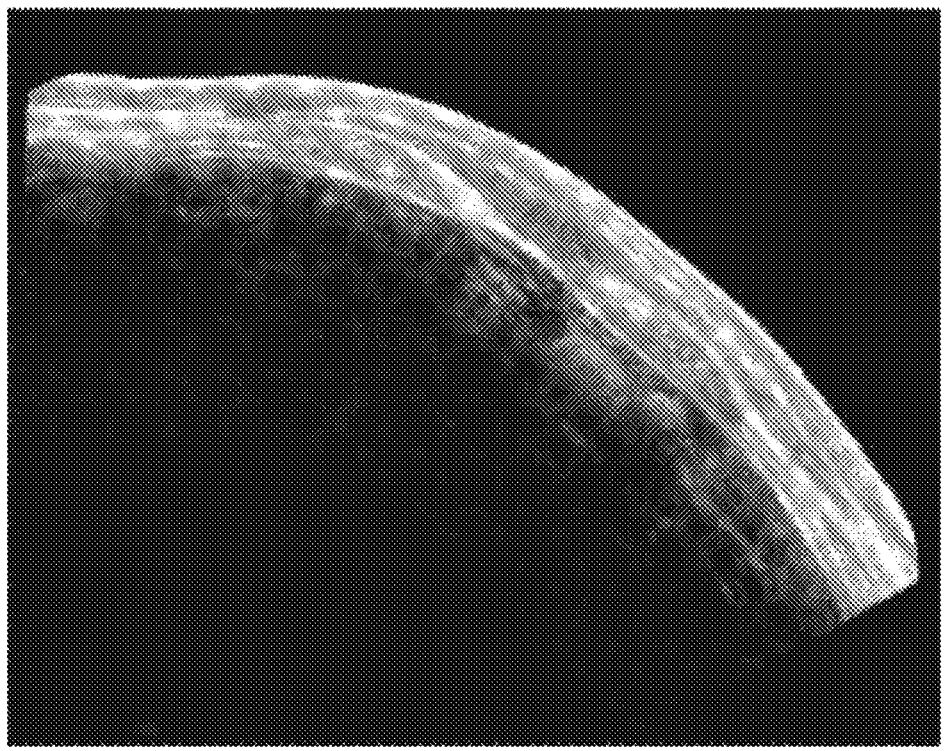
FIG. 3 is an example of an ultrasound stitched image of an abdominal section.

In the present embodiment, it is assumed that an ultrasound stitched image including the abdominal section shown in FIG. 3 is generated.

The rotation angle adjusting module 352, the reference point setting module 353, the first seed point imparting module 354, and the region demarcation module 355 are functional blocks that divide the image region of the analyte included in the ultrasound stitched image into a plurality of regions according to the type of tissue. The type of tissue is not particularly limited, but when the subject is an abdomen, the type of tissue is 3 types of muscle, skin, and other tissues (fat, etc.), and the image region of the subject included in the ultrasound stitched image is divided into a plurality of regions according to the skin, muscle, and other tissues, and is displayed in a distinguishable manner (for example, in different colors) in each region. A specific method of region division will be described later.

The divided ultrasound stitched image is input to the display interface module 36. The display interface module 36 displays the ultrasound stitched image on the display 31 by developing the data of the ultrasound stitched image in a Video Random Access Memory (VRAM). It should be noted that the display interface module 36 may display the ultrasound stitched image on the display 31 once before performing the following region division, or may display the ultrasound stitched image on the display 31 after performing the region division.

Hereinafter, an embodiment of dividing an image region of the analyte included in an ultrasound stitched image into a plurality of regions according to the type of tissue will be described in detail.

The rotation angle adjusting module 352 has a function of adjusting the angle of the ultrasound stitched image and directing a specific portion of the subject included in the ultrasound stitched image in a predetermined direction. In the present embodiment, the rotation angle adjusting module 352 adjusts the direction of the ultrasound stitched image shown in FIG. 3 so that the navel portion faces upward as in the ultrasound stitched image shown in FIG. 4. A specific method of adjustment will be described later.

The reference point setting module 353 is a functional block for setting the reference point of the tissue of interest of the ultrasound image. The reference point is a point serving as a reference for imparting a seed point, and is preferably included in a part having a characteristic shape in a standard living body, and the kind of tissue at a predetermined relative position to the point can be specified in the standard living body. The tissue of interest refers to a region having a characteristic (unique) shape that appears in only one portion of the analyte included in the ultrasound stitched image. In the present embodiment, as shown in a broken line frame in FIG. 4, a portion including a portion of a pair of right and left rectus abdominis muscles and a "white line" existing between the rectus abdominis muscles is regarded as a tissue of interest.

Figure 4:
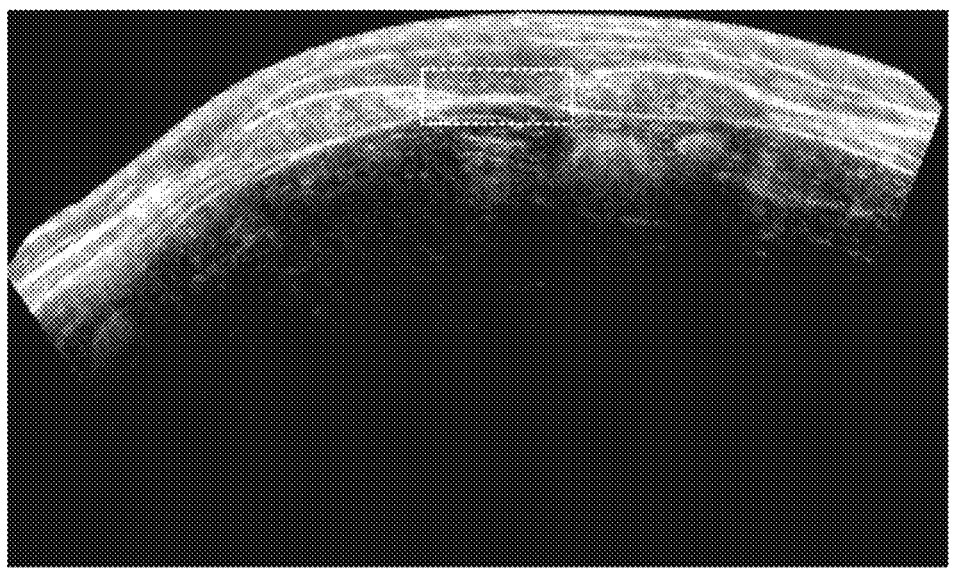
FIG. 4 is an example of a rotation angle adjusted ultrasound stitched image.

The "white line" is a strong, string-like connective tissue formed by the fibers of the aponeurosis of the lateral abdominal muscles, which form the anterior and posterior lobes of the rectus sheath, intermingling with each other in the midline of the anterior abdominal wall. As shown in FIG. 4, the ultrasound stitched image of the abdominal section is adjusted so that the navel portion is in the upward direction, and the "white line" is indicated by a high brightness line segment extending horizontally, and both ends of the line segment are branched in two directions. In the present embodiment, the midpoint of the "white line" is used as the reference point. In a typical abdomen with the navel portion pointing upward, the rectus abdominis muscle contains a location that is a predetermined distance laterally from the midpoint of the "white line", the skin contains a location that is a predetermined distance upward, and other tissues, such as fat, contain a location that is a predetermined distance downward.

Figure 5:
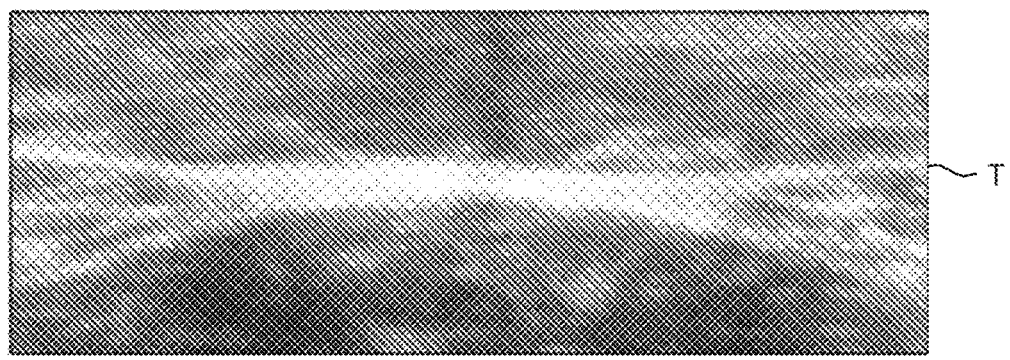
FIG. 5 is an example of a template image.

In order to set a reference point in the ultrasound stitched image shown in FIG. 4, the reference point setting module 353 matches the template image T while superimposing it on the ultrasound stitched image. FIG. 5 shows an example of the template image T. The template image T is an ultrasound synthesized image including a part of a pair of right and left rectus abdominis muscles and "white line" existing between the rectus abdominis muscles, but the template image T is not particularly limited as long as it is an ultrasound synthesized image including a part having a characteristic shape in a standard living body. The template image T can be created by averaging the aforementioned portions of a plurality of individuals. Alternatively, if an ultrasound stitched image of the same subject has been generated in the past, the above-described portion in the ultrasound stitched image of the analyte in the past may be used as the template image T.

Figure 6:
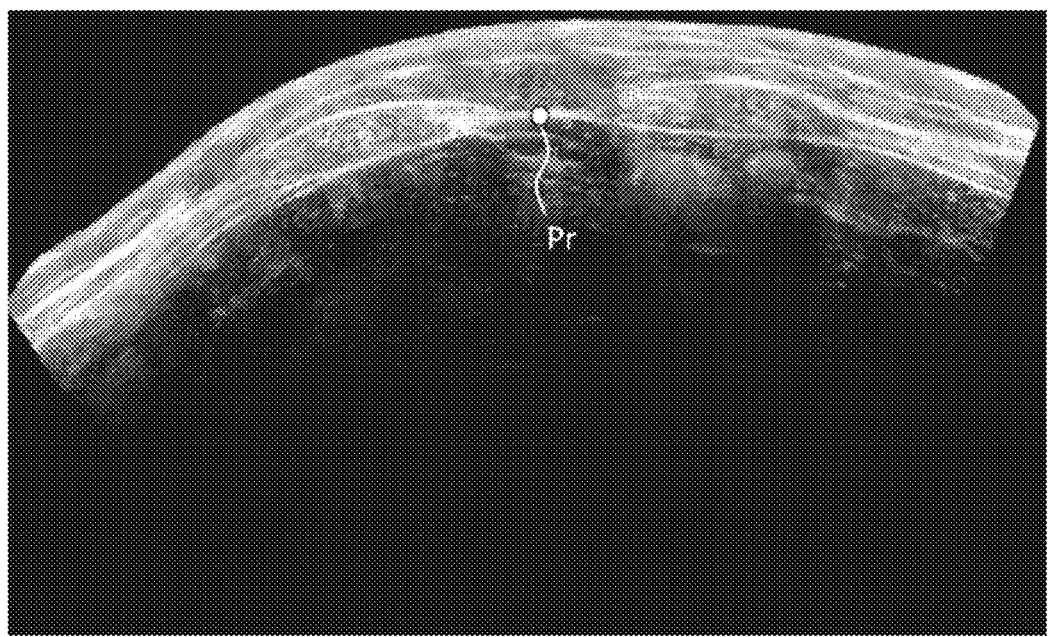
FIG. 6 is an example of an ultrasound stitched image with a reference point set.

The reference point setting module 353 virtually moves the template image T on the ultrasound stitched image shown in FIG. 4, and specifies a position on the ultrasound stitched image having the highest correlation with the template image T. Since the template image T includes the tissue of interest in the standard living body, only the region shown by the broken line frame in FIG. 4 is necessarily specified. Further, as shown in FIG. 6, the reference point setting module 353 sets the midpoint of "white line" as the reference point Pr. Note that the reference point is a virtual one, and it is not necessary to display it as a point as shown in FIG. 6.

Figure 7:
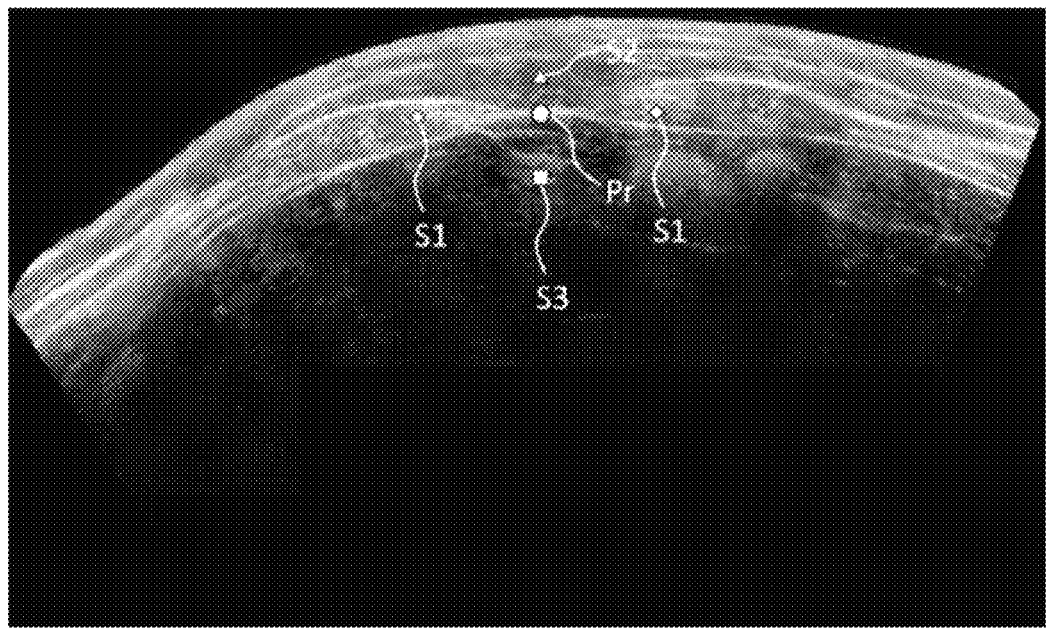
FIG. 7 is an example of a seeded ultrasound stitched image.

The first seed point imparting module 354 is a functional block for imparting one or more seed points in the ultrasound stitched image on the basis of the reference point set by the reference point setting module 353, and the seed points are imparted at predetermined relative positions to the reference point. The predetermined relative position means a position at a predetermined distance and a predetermined direction away from the reference point in the ultrasound stitched image. In the present embodiment, as shown in FIG. 7, the first seed point imparting module 354 imparts a seed point S1 at two positions of the specified distance (for example, 4 cm) in the lateral direction (two directions perpendicular to a given direction) away from a reference point Pr in association with the muscle, imparts a seed point S2 at the specified distance (for example, 1 cm) in the upward direction away from the reference point Pr in association with the skin, and imparts a seed point S3 at the specified distance (for example, 3 cm) in the downward direction away from the reference point Pr in association with other tissues. The correspondence between the position of the seed point and the tissue is based on the fact, that the rectus abdominis muscle exists in the lateral direction, the skin exists in the upper direction, and other tissues such as fat exist in the lower direction with respect to the midpoint of "white line" which is a reference point in a standard organism. Therefore, as long as the structure of the analyte 9 is not substantially different from the structure of a standard living body, the seed point can be accurately correlated with the type of tissue.

The region demarcation module 355 is a functional block that demarcates a region to which the seed point belongs and divides the image region of the analyte 9 included in the ultrasound stitched image into a plurality of regions according to the type of tissue. In the present embodiment, the region demarcation module 355 refers to the region demarcation information V stored in the auxiliary storage 33 shown in FIG. 2. The region demarcation information V is information indicating the correspondence between the specific position of the tissue of interest and the type of tissue at a predetermined relative position from the tissue of interest. In the region demarcation information V, for example, when the tissue of interest is "white line" and the navel portion in the ultrasound stitched image is in the upward direction, a position apart from the midpoint of the "white line" by a specified distance (for example, 4 cm.) in the lateral direction is associated with the muscle, a position apart from the specified distance (for example, 1 cm.) in the upward direction is associated with the skin, and a position apart from the specified distance (for example, 3 cm.) in the downward direction is associated with the other tissue. Thus, the region demarcation module 355 can determine that the tissues corresponding to the seed points S1, S2, and S3 are muscles, skin, and other tissues based on the region demarcation information V.

Figure 8:
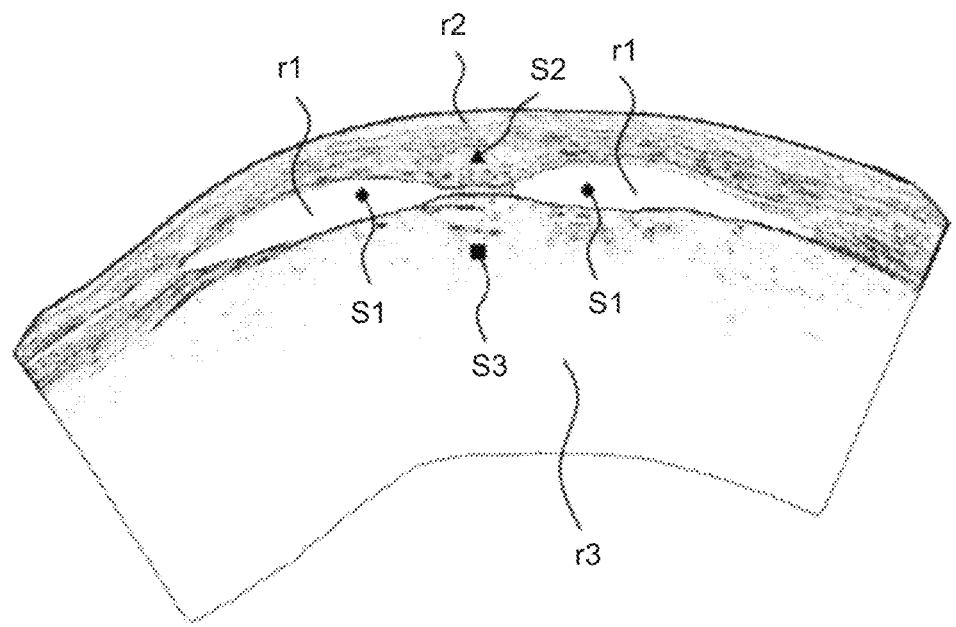
FIG. 8 is an example of an ultrasound stitched image divided into different regions.

Further, the region demarcation module 355 uses, for example, Grow Cut techniques to demarcate a muscle region r1 based on the seed point S1, a skin region r2 based on the seed point S2, and other tissue regions r3 based on the seed point S3, as shown in FIG. 8. In FIG. 8, the regions r1, r2, and r3 are shown in different shades, but the display mode of the regions is not particularly limited, and may be shown in different colors (for example, region r1=red, region r2=blue, region r3=green). In this way, the analyte included in the ultrasound stitched image generated by the image stitcher 3512 can be divided into a plurality of regions r1 to r3 according to the type of tissue.

Thereafter, the region demarcation module 355 outputs the data of the ultrasound stitched image to the display interface module 36. In response to this, the display interface module 36 displays the ultrasound stitched image on the display 31 in such a manner that the divided regions r1 to r3 can be identified (for example, in different colors). Thus, the subject can obtain an ultrasound stitched image in which the image region of the subject is divided into a plurality of regions according to the type of tissue without imparting a seed point to the ultrasound stitched image by himself, and can intuitively grasp the state of the abdomen.

The cross-sectional area may be automatically calculated for each of the regions r1 to r3, and the amount of muscle, fat percentage, and the like may be displayed on the display 31.

In the present embodiment, the image region of the subject is divided into three regions of muscle, skin, and other tissues, but the type of tissue and the number of regions is not particularly limited. For example, when only the muscle amount is to be grasped, the image region of the subject may be divided into two regions of the muscle and the other tissue. In this case, the first seed point imparting module 354 imparts only the seed point S1 in the ultrasound stitched image shown in FIG. 7, and the region demarcation module 355 may demarcate only the region to which the seed point S1 is imparted in a manner distinguishable from other regions.

Figure 9:
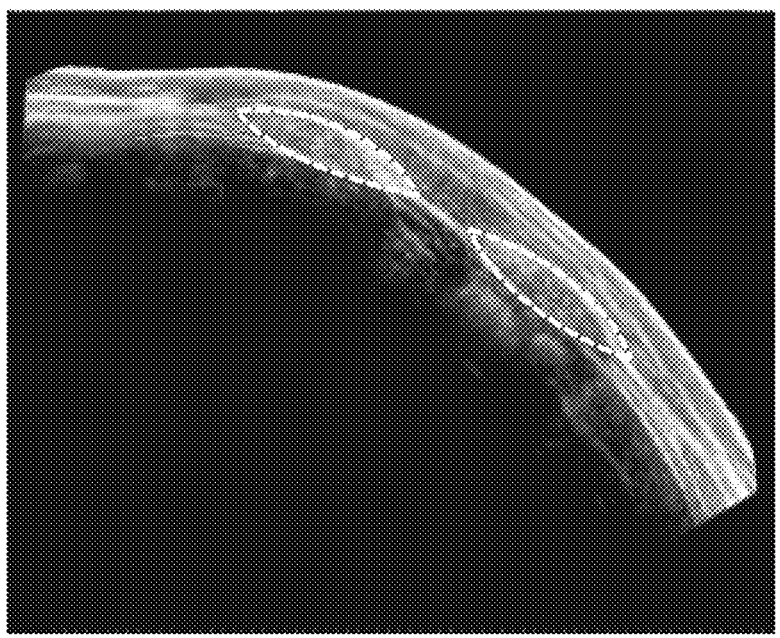
FIG. 9 is an example of an ultrasound stitched image of an abdominal section.

Hereinafter, an embodiment in which the rotation angle adjusting module 352 adjusts the direction of the ultrasound stitched image will be specifically described. In the present embodiment, as shown by a broken line in FIG. 9, the orientation of the ultrasound stitched image is adjusted so that the navel portion is in a predetermined direction (for example, upward) by utilizing the fact that the cross-sectional shape of the rectus abdominis muscle is approximately symmetrical.

Figure 10:
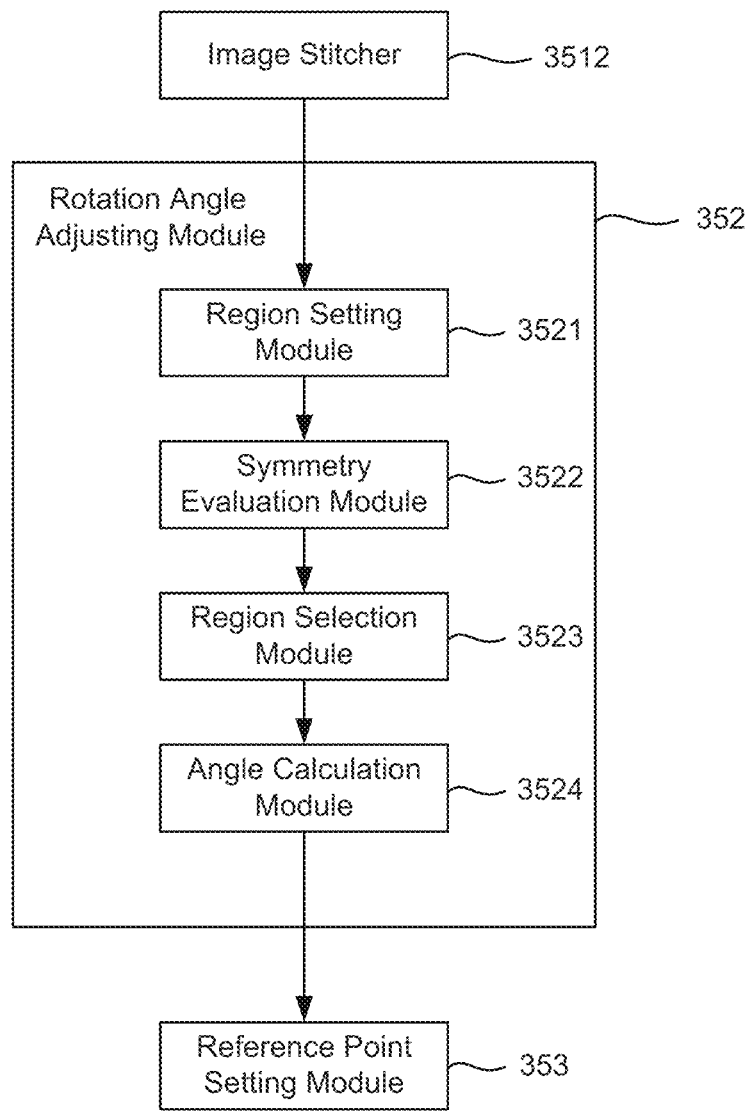
FIG. 10 is a functional block diagram of a rotation angle adjustment module.

As shown in FIG. 10, the rotation angle adjusting module 352 includes a region setting module 3521, a symmetry evaluation module 3522, a region selection module 3523, and an angle calculation module 3524.

The region setting module 3521 is a functional block for setting one or a plurality of regions of interest r having a shape of line symmetry with respect to the central axis at an arbitrary position and an arbitrary angle. In the present embodiment, the shape of the region of interest r is a rectangle linearly symmetrical with respect to the central axis Ax, as shown by a white line in FIG. 11. If the region of interest r contains the right and left rectus abdominis equally, then the central axis Ax of the region of interest r can be considered the central axis through the navel portion. The region setting module 3521 sets the region of interest r to be movable in order to search for the region of interest r having high left-right symmetry.

Figure 12:
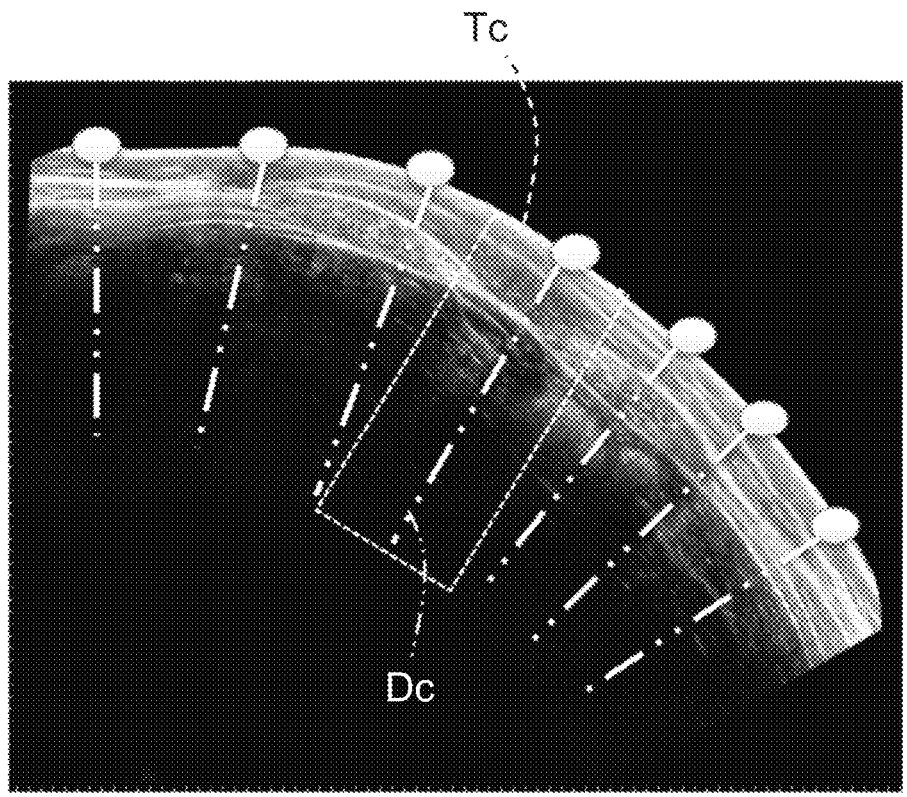
FIG. 12 is an illustration of the track of the probe and the ultrasound transmission direction.

More specifically, the region setting module 3521 selects one ultrasound image from a plurality of ultrasound images used for generating the ultrasound stitched image, and sets the region of interest r by aligning the central axis Ax of the region of interest r with an axis indicating the transmission direction of the ultrasound wave at a position on the surface of the analyte 9. Accordingly, the region setting module 3521 sets each region of interest r by aligning the center axis Ax of each region of interest r with each axis indicating the transmission direction of ultrasound waves at a plurality of different positions on the surface of the analyte 9. The transmission direction of the ultrasound wave in each ultrasound image can be specified based on the homogeneous transformation matrix to the coordinate system of the first ultrasound image (world coordinate system). The track of the probe 2 at the time of acquiring the ultrasound image corresponds to the upper side of each ultrasound image. Therefore, as shown in FIG. 12, the track of the probe 2 and information on the transmission direction of the ultrasound wave are included in the ultrasound stitched image.

The region setting module 3521 may sequentially select from the first ultrasound image to the n-th ultrasound image, but in the present embodiment, the central axis of the central ultrasound image corresponding to the center of the order in which the ultrasound image is generated and the central axis of the central ultrasound image in a predetermined number of generation orders before and after the central ultrasound image are sequentially selected. If n is an even number, the central ultrasound image corresponds to the n/2-th ultrasound image. When n is an odd number, the central ultrasound image corresponds to either the (n−1)/2-th or the (n+1)/2-th ultrasound image. The axis indicating the transmission direction of the ultrasound wave in the central ultrasound image is referred to as Dc. The region setting module 3521 first selects a central ultrasound image from the n ultrasound images, and sets the region of interest r by matching the axis Dc of the central ultrasound image with the central axis Ax of the region of interest r indicated by a chain line in FIG. 11. That is, the region of interest r in which the central axis coincides with the transmission direction of the ultrasound wave in the central ultrasound image is set as the search start region. In the following description, when the transmission direction of the ultrasound wave in the ultrasound image coincides with the central axis of the region of interest, the ultrasound image corresponds to the region of interest.

Thereafter, when the region of interest r is moved, the region setting module 3521 selects another ultrasound image, and sets the region of interest r again so that the transmission direction of the ultrasound wave in the selected ultrasound image coincides with the central axis Ax of the region of interest r. In the present embodiment, after selecting the central ultrasound image Tc, the region setting module 3521 sequentially selects a predetermined number m of ultrasound images (Ultrasound images from (n/2−m/2)-th to (n/2+m/2−1)-th when m is even) before and after the central ultrasound image Tc in the order of generation, thereby moving the region of interest r.

When the subject acquires an ultrasound image of the abdomen, the probe 2 is normally moved from the vicinity of one side of the abdomen to the vicinity of the other side of the abdomen via the navel portion. Therefore, there is a high possibility that the position of the probe 2 at the time of obtaining the central ultrasound image Tc is near the navel portion. Therefore, the search for the region of interest r having a high left-right symmetry need not be performed for the regions of interest corresponding to all the ultrasound images, and m<n is possible. Thus, the number of times of movement of the region of interest r is suppressed, and the amount of computation can be reduced.

Figure 11:
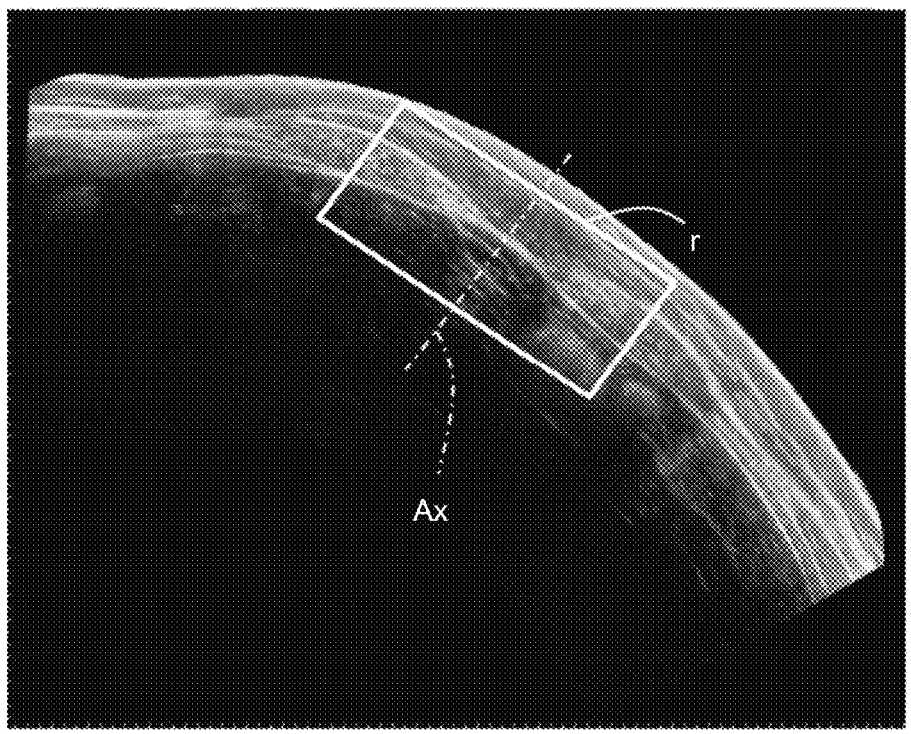
FIG. 11 is an example of an ultrasound stitched image in which a region of interest is set.

The symmetry evaluation module 3522 shown in FIG. 10 is a functional block for evaluating the degree of symmetry of each of the left and right images in the region of interest r with respect to the central axis Ax of the region of interest r. For example, when the region of interest r shown in FIG. 11 is set, the symmetry evaluation module 3522 evaluates the symmetry degree of the region of interest r by calculating a correlation value between the region on the left side and the region on the right side with respect to the central axis Ax. As the calculation method of the correlation value, for example, Sum of Absolute Difference (SAD), Sum of Squared Difference (SSD), Normalized Cross-Correlation (NCC), and Zero-means Normalized Cross-Correlation (ZNCC) can be used, but ZNCC which is robust against changes in brightness is particularly preferred.

In the ultrasound stitched image, the boundary between the muscle such as the rectus abdominis and the other tissue becomes high brightness, so that a linear pattern is formed. Preferably, the symmetry evaluation module 3522 calculates a correlation value of a pattern in the region of interest r.

Instead of the correlation value, a mutual information may be used to evaluate the left-right symmetry.

Figure 13:
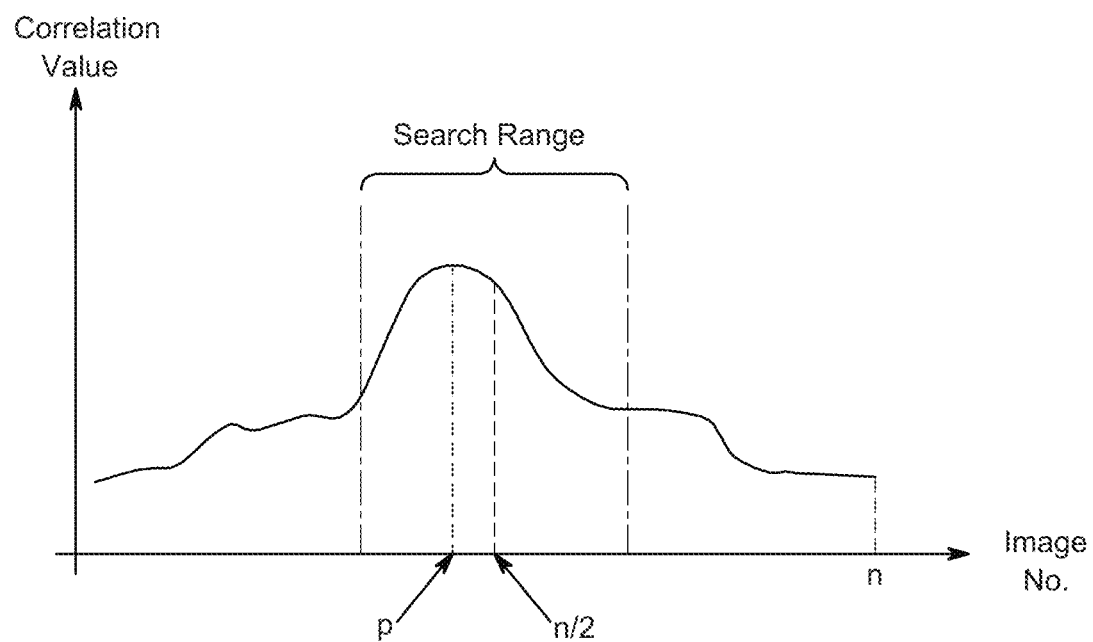
FIG. 13 is a graph showing an example of the relationship between the numbers of ultrasound images corresponding to regions of interest and correlation values.

The symmetry evaluation module 3522 evaluates the left-right symmetries of all the regions of interest r set by the region setting module 3521, and records the left-right symmetries in the memory each time the region of interest r moves. FIG. 13 is a graph showing an example of the relationship between the ultrasound image number (Image No.) corresponding to the region of interest and the correlation value.

Figure 14:
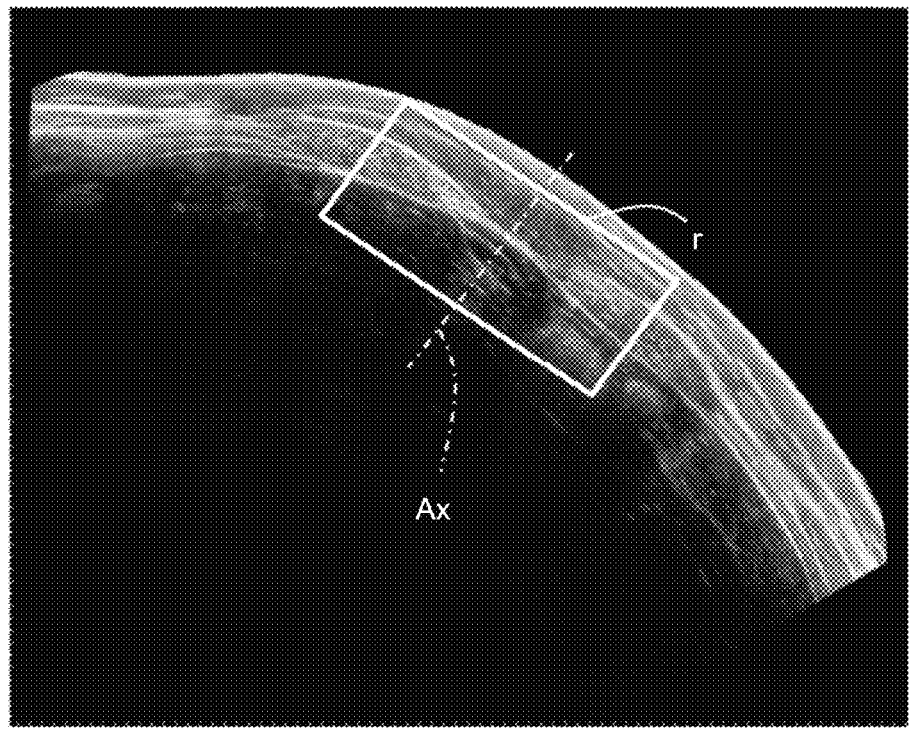
FIG. 14 is an example of an ultrasound stitched image in which a region of interest is set approximately in the middle of the rectus abdominis.

The region selection module 3523 is a functional block for selecting the region of interest r on the basis of the left-right symmetry. In this embodiment, the region selection module 3523 selects the region of interest r having the highest degree of left-right symmetry from the regions of interest r whose left-right symmetry has been evaluated (in the example shown in FIG. 13, a region of interest corresponding to the p-th ultrasound image). As a result, as shown in FIG. 14, the region of interest r in which the central axis Ax is located in the middle of the right and left rectus abdominis muscles is selected.

The region of interest selected by the region selection module 3523 need not necessarily be a region of interest having the maximum degree of symmetry, but may be any region of interest having a degree of symmetry equal to or greater than a predetermined threshold value. For example, a region of interest having a relatively high degree of left-right symmetry, such as a region of interest having a second highest degree of left-right symmetry, may be selected.

The angle calculation module 3524 is a functional block for calculating an angle difference between a predetermined axis passing through the ultrasound stitched image and the central axis Ax of the selected region of interest r, and the rotation angle adjusting module 352 adjusts the angle of the ultrasound stitched image based on the angle difference calculated by the angle calculation module 3524. In the present embodiment, the predetermined axis passing through the ultrasound stitched image is the left-right symmetry axis of the ultrasound stitched image. As a result, the ultrasound stitched image is rotated so that the central axis Ax shown in FIG. 14 is directed upward, and the ultrasound stitched image in which the navel portion is directed upward is generated as shown in FIG. 4.

Figure 15:
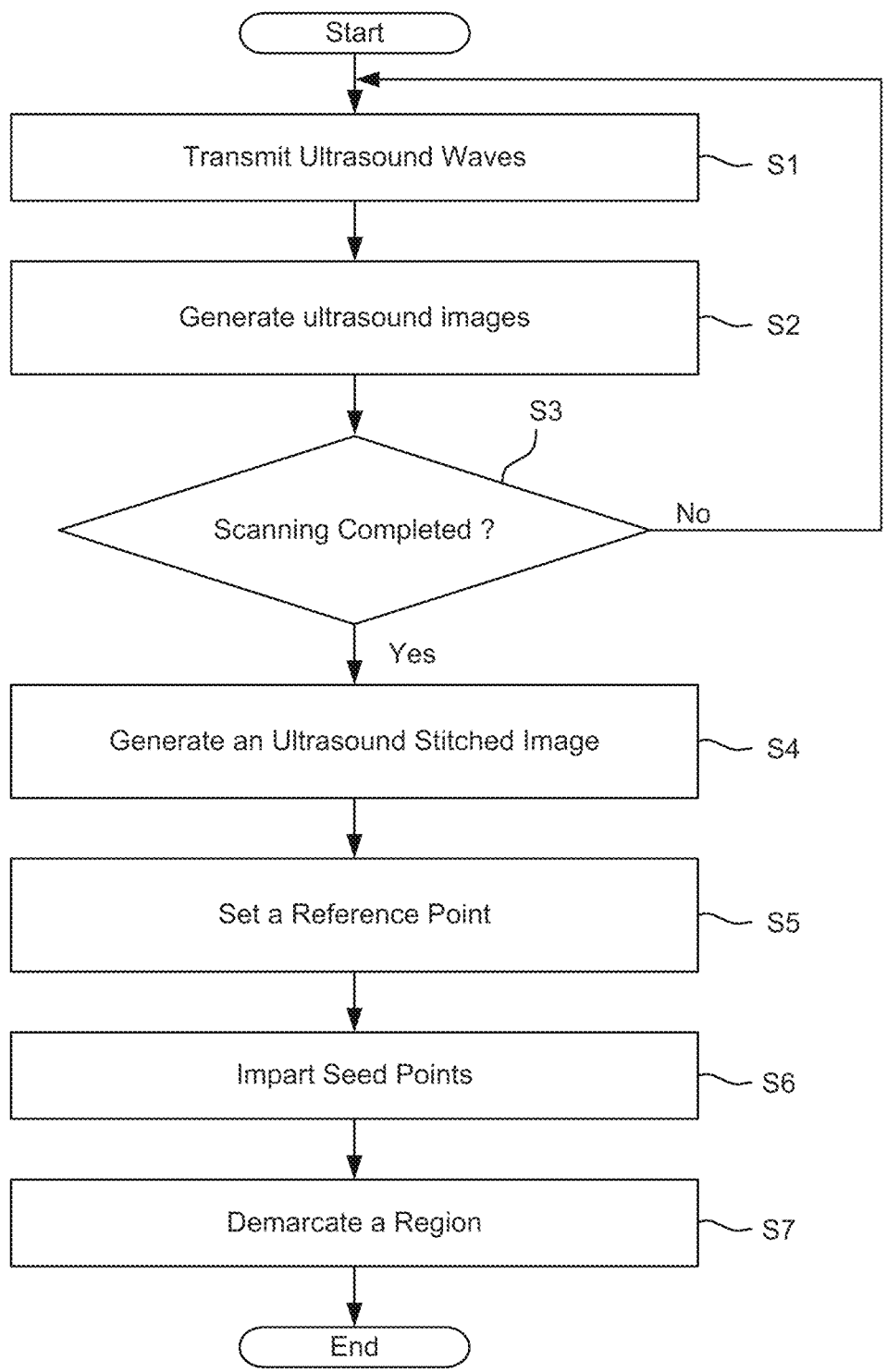
FIG. 15 is a flowchart showing a processing procedure of the ultrasound imaging method according to the first embodiment.

FIG. 15 is a flowchart showing the processing procedure of the ultrasound imaging method according to the present embodiment.

In step S1, the probe 2 transmits ultrasound waves from a plurality of mutually different positions on the surface of the analyte 9 toward the inside of the analyte 9. Thus, the probe 2 receives the ultrasound wave reflected inside the analyte 9 and outputs an echo signal from the probe 2.

In step S2, the ultrasound image generation module 3511 generates ultrasound images corresponding to a plurality of mutually different positions on the surface of the analyte 9. In this embodiment, each time an echo signal is output from the probe 2, the ultrasound image generation module 3511 generates an ultrasound image. At step S3, it is checked if the scanning of the probe 2 is completed, and steps S1 and S2 are repeated until the scanning of the probe 2 is completed.

When the scanning of the probe 2 is completed, in step S4 (image generation step), the image stitcher 3512 stitches the ultrasound images at the respective positions to generate an ultrasound stitched image of the cross section of the analyte 9.

Subsequently, in step S5 (reference point setting step), the reference point setting module 353 sets a reference point of the tissue of interest of the ultrasound stitched image.

Then, in step S6 (seed point imparting step), the first seed point imparting module 354 imparts one or more seed points in the ultrasound stitched image with the reference point as a reference.

Thereafter, in step S7 (region demarcating step), the region demarcation module 355 demarcates a region to which the seed point belongs, and divides the image region of the analyte included in the ultrasound image into a plurality of regions according to the type of tissue.

As described above, in the present embodiment, by matching the template image T including a portion of a pair of right and left rectus abdominis muscles and a "white line" existing between the rectus abdominis muscles with the ultrasound stitched image, the midpoint of the "white line" is set as a reference point Pr, and seed points are imparted in association with the type of tissue on the basis of the reference point Pr, thereby demarcating a region to which each seed point belongs. In this way, since the boundary of the biological tissue can be automatically detected in the ultrasound stitched image, the burden on the user can be reduced by saving the time and effort for the subject (users) to manually add the seed point.

Figure 16:
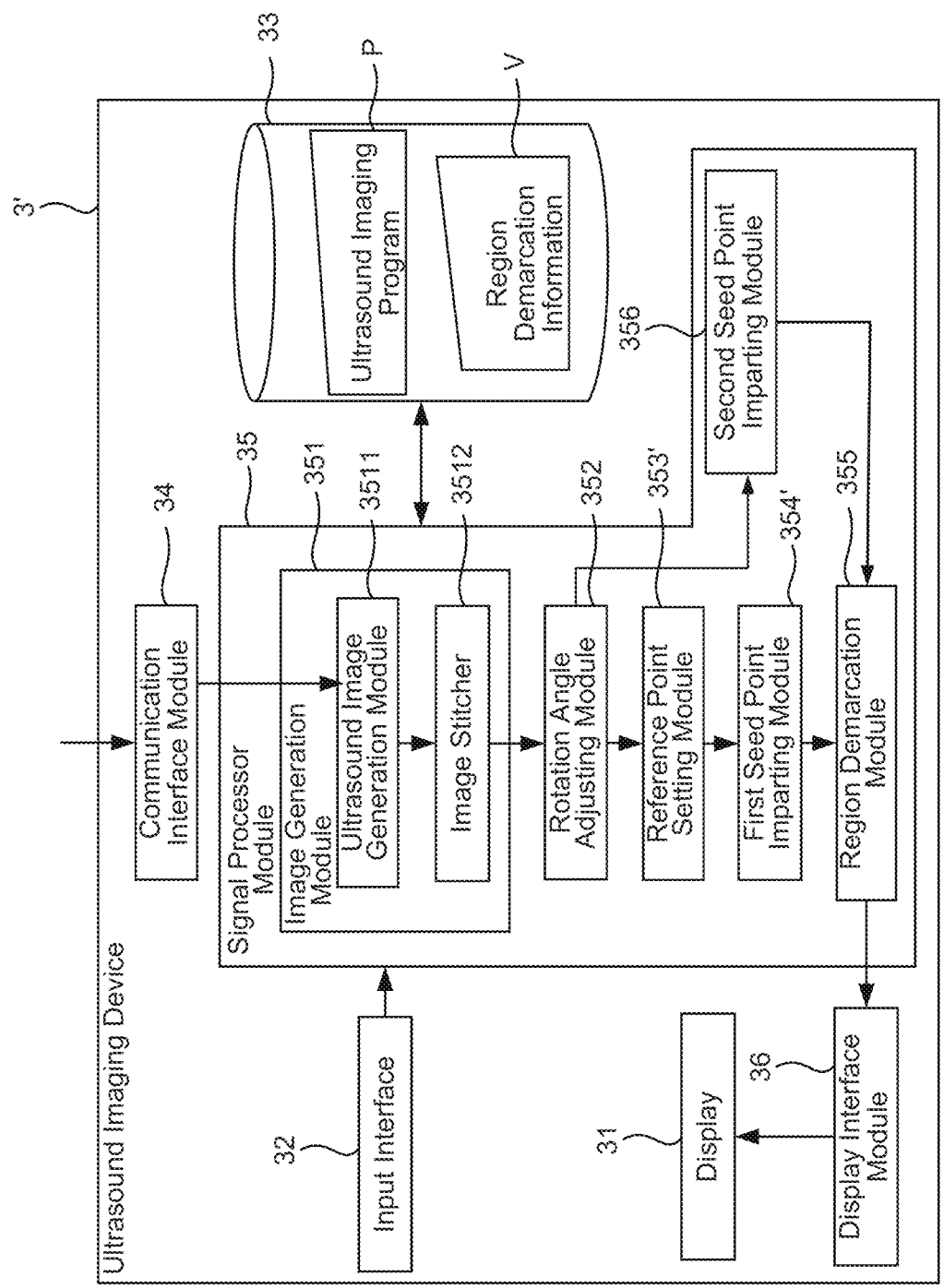
FIG. 16 is a block diagram showing a configuration of an ultrasound imaging device according to a second embodiment.

In the second embodiment, a method of setting a reference point and imparting a seed point in a manner different from that of the first embodiment will be comprehensively described. FIG. 16 is a block diagram showing the configuration of the ultrasound imaging device 3' according to the second embodiment. In the ultrasound imaging device 3 shown in FIG. 2, the reference point setting module 353 and the first seed point imparting module 354 are replaced with the reference point setting module 353' and the first seed point imparting module 354', respectively, and the second seed point imparting module 356 is further provided. The template image T is not stored in the auxiliary storage 33.

Similarly to the first embodiment, the rotation angle adjusting module 352 adjusts the direction of the ultrasound stitched image shown in FIG. 3 so that the navel portion faces upward as shown in the ultrasound stitched image shown in FIG. 4.

The reference point setting module 353' is a functional block for setting a reference point in the ultrasound stitched image as in the reference point setting module 353 in the first embodiment, but is different from the reference point setting module 353 in that a template image is not used. In the present embodiment, the reference point setting module 353' sets the position with the largest luminance value on the line extending in the transmission direction of the ultrasound wave through the navel portion as the reference point Pr. The luminance value is a concept including a value of a pixel value (original data) corresponding to luminance in an ultrasound image displayed on a display or the like.

As described in the first embodiment, as shown in FIG. 14, the rotation angle adjusting module 352 searches for the region of interest r having the highest left-right symmetry in the ultrasound stitched image, and adjusts the ultrasound stitched image so that the central axis Ax of the region of interest r faces upward. That is, the central axis Ax shown in FIG. 14 forms a line extending in the transmission direction of ultrasound waves through the navel portion. Since the position where the line crosses "white line" has the highest luminance on this line, the reference point setting module 353' sets the position where the luminance value is the highest on the line (Highest filter value with convex filter) as the reference point Pr. Thus, as in the first embodiment, the midpoint of the "white line" can be used as the reference point Pr.

It should be noted that the reference point setting module 353' is not necessarily required to set the position with the largest luminance value on the line as the reference point Pr, and any of the positions with luminance values equal to or higher than a predetermined threshold value on the line may be set as the reference point Pr. For example, a position having the second largest luminance value on the line may be set as the reference point Pr.

The first seed point imparting module 354' is a functional block for imparting a seed point in the ultrasound stitched image in association with the type of the tissue based on the reference point in the same manner as the first seed point imparting module 354 in the first embodiment, but is different from the first seed point imparting module 354 in that a Dijkstra method is used. In the present embodiment, the first seed point imparting module 354' searches two pathways with the reference point Pr as a search starting point and a line crossing from the front side to the rear side of the rectus abdominis as a search end point by the Dijkstra method, and imparts a seed point to a region sandwiched between the searched two pathways.

Figure 17:
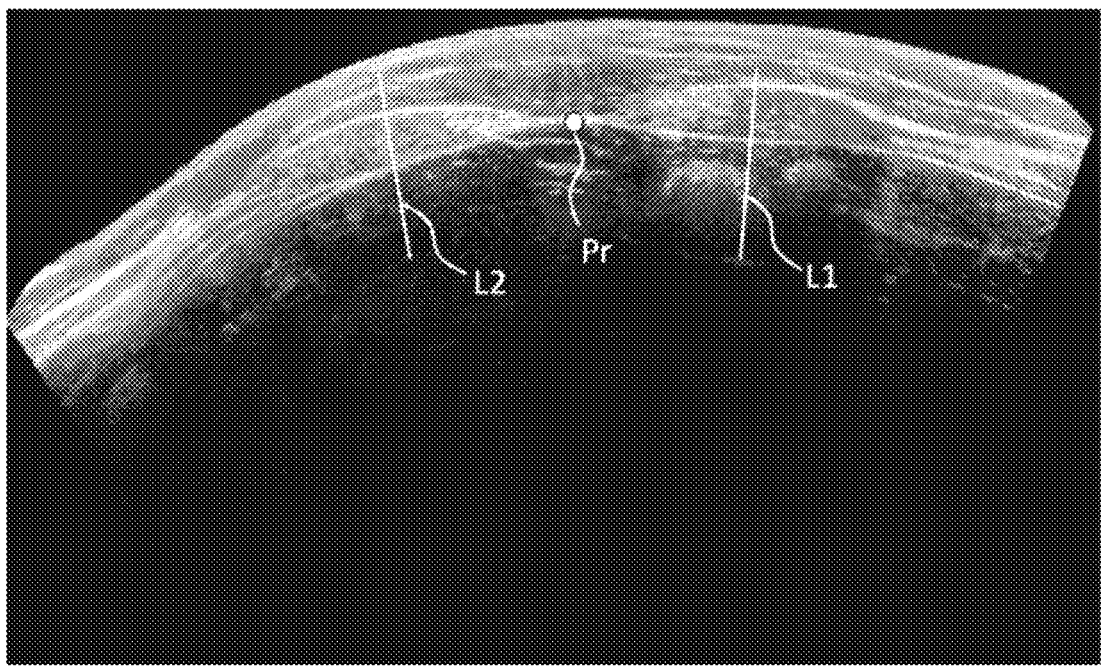
FIG. 17 is an example of an ultrasound stitched image with reference points and lines.

Specifically, as shown in FIG. 17, the first seed point imparting module 354' sets lines L1 and L2 crossing from the front side to the rear side of the rectus abdominis. In the present embodiment, the lines L1 and L2 are straight lines extending substantially in the vertical direction separated by a predetermined distance to the left and right of the reference point Pr. More specifically, a line L1 is aligned with the transmission direction of the ultrasound wave in the ultrasound image after a predetermined frame from an ultrasound image in which the transmission direction of an ultrasound wave coincides with the central axis Ax shown in FIG. 14 (central ultrasound image), and a line L2 is aligned with the transmission direction of the ultrasound wave in the ultrasound image before the predetermined frame from the central ultrasound image (assume the scan direction is from upper left to lower right). The positions of the lines L1 and L2 are preferably set so as to cross the central portion of the rectus abdominis muscle having the largest thickness, but the positions are not particularly limited as long as they cross from the front side to the back side of the rectus abdominis muscle.

Since luminance is high near the skin of the ultrasound stitched image, it is desirable that the lines L1 and L2 do not reach near the skin. The lines L1 and L2 may be parallel straight lines extending in the vertical direction.

Figure 18:
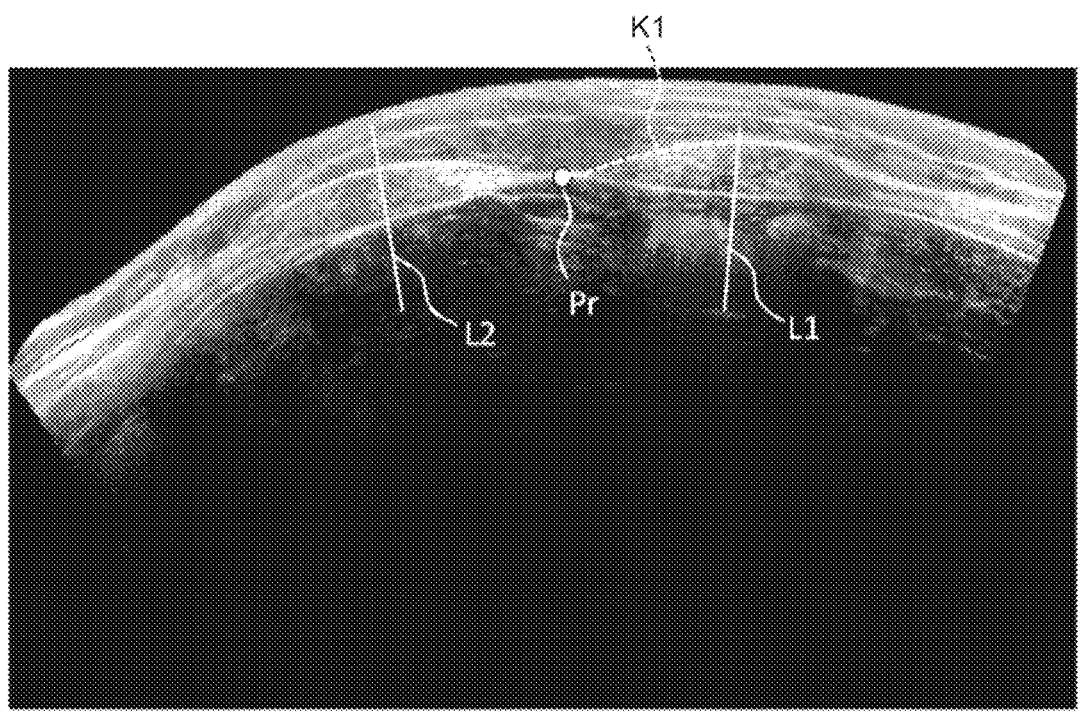
FIG. 18 illustrates a Dijkstra method search.
Figure 19:
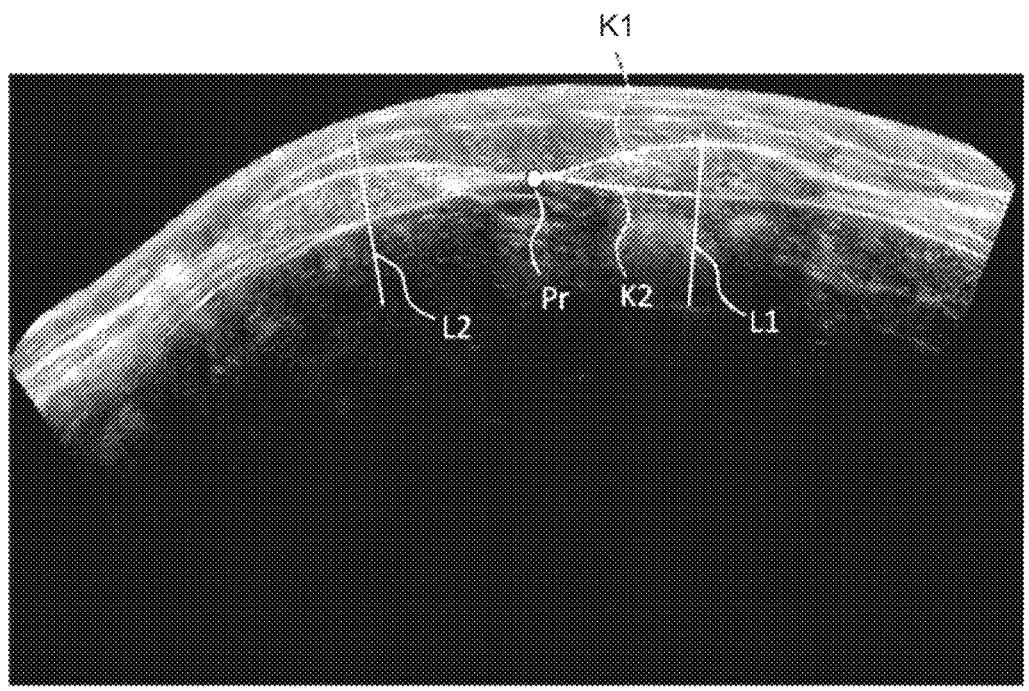
FIG. 19 illustrates a Dijkstra method search.

Subsequently, as shown in FIG. 18, the first seed point imparting module 354' searches one path K1 with the reference point Pr as a search starting point and the line L1 as a search end point by the Dijkstra method. The conditions of the search are, for example, high total luminance value in the path (static condition)
a gradual arc (dynamic condition)

are listed. Since the fascia of the rectus abdominis has a large luminance value, the pathway K1 is a curve tracing from "white line" to either the front or back fascia of the rectus abdominis (front fascia in FIG. 18). Further, the first seed point imparting module 354' performs a search by the Dijkstra method under the same conditions as described above, and as shown in FIG. 19, searches for another pathway K2 whose search start point is the reference point Pr and whose search end point is on the line L1. Pathway K2 is a curve that follows the fascia of the back of the rectus abdominis muscle from "white line".

Figure 20:
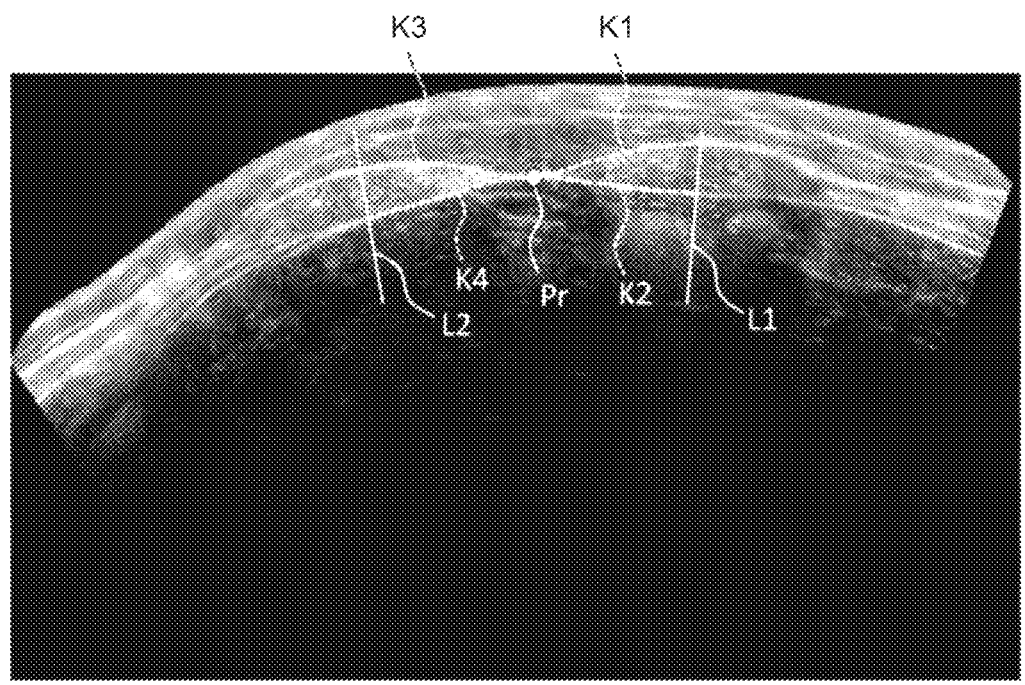
FIG. 20 illustrates a Dijkstra method search.

Thereafter, as shown in FIG. 20, the first seed point imparting module 354' searches the two pathways K3 and K4 with the reference point Pr as a search starting point and the line L2 as a search end point by the same method.

Further, the first seed point imparting module 354' imparts a seed point to a region sandwiched between the two pathways K1 and K2 (region surrounded by pathways K1, K2 and line L1) in association with a muscle. Although the number of seed points to be imparted is not particularly limited, it is preferable to impart as many seed points as possible. Similarly, the first seed point imparting module 354' imparts a seed point in a region sandwiched between the two pathways K3, K4 (region surrounded by pathways K3, K4 and line L2) in association with a muscle.

As shown in FIG. 7, the first seed point imparting module 354 in the first embodiment imparts a seed point S1 corresponding to a muscle to only the left and right two points of the reference point Pr. On the other hand, the first seed point imparting module 354' according to the second embodiment can apply a large number of seed points corresponding to muscles over a wide range. Therefore, the accuracy of the region demarcating processing by the region demarcation module 355 described later can be improved and the processing time can be shortened.

The second seed point imparting module 356 is a functional block that selects at least one ultrasound image from a plurality of ultrasound images for generating an ultrasound stitched image, imparts a seed point corresponding to the skin at a position on the ultrasound stitched image corresponding to any position on the upper end of the selected ultrasound image, and imparts a seed point corresponding to tissue other than the skin and muscle at a position on the ultrasound stitched image corresponding to any position on the lower end of the selected ultrasound image. The second seed point imparting module 356 is different from the first seed point imparting module 354 and the first seed point imparting module 354' in that seed points can be imparted without using the reference point Pr.

Figure 21:
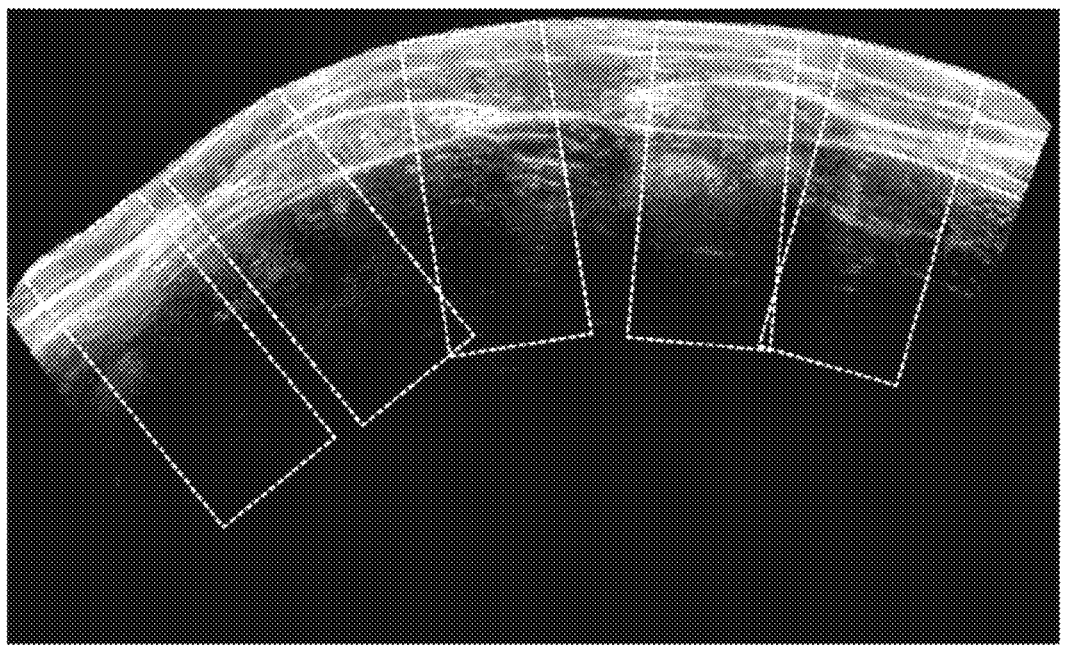
FIG. 21 is an example of an ultrasound stitched image showing a range of ultrasound images.

The ultrasound stitched image is a composite of a plurality of ultrasound images, and as shown by a plurality of rectangular frames in FIG. 21, information on the range of each ultrasound image is included in the ultrasound stitched image. In FIG. 21, five rectangular frames are shown, which are extracted from an ultrasound image used for generating an ultrasound stitched image. The upper end of each ultrasound image corresponds to the abdominal epidermis in contact with the probe during scanning, and the lower end of each ultrasound image corresponds to tissue deep in the abdomen (fats and other than skin and muscle).

Figure 22:
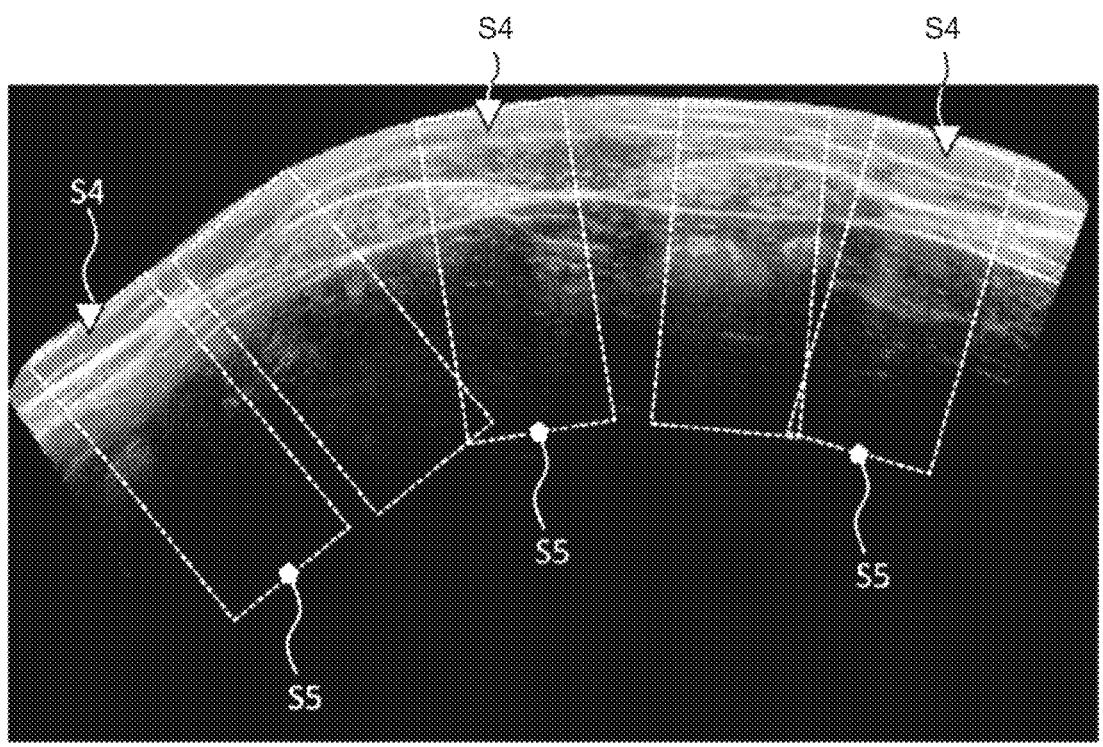
FIG. 22 shows an example of a seeded ultrasound stitched image.

Therefore, as shown in FIG. 22, for example, the second seed point imparting module 356 in the second embodiment selects three ultrasound images and imparts a seed point S4 to the position of the midpoint of the upper end of the ultrasound images in association with the skin. Similarly, the second seed point imparting module 356 imparts a seed point S5 to the position of the middle point of the lower end of the selected three ultrasound images in association with the tissues other than the skin and the muscle. Although the number of ultrasound images to be selected is not particularly limited, it is preferable to select all the ultrasound images from the viewpoint of providing more seed points. As described above, the second seed point imparting module 356 can automatically impart seed points corresponding to the skin and the tissues other than the skin and the muscle without using the reference point Pr. The first seed point applying module 354' can apply a seed point corresponding to the muscle on the ultrasound synthesized image as described above. That is, the first seed point imparting module 354' and the second seed point imparting module 356 can impart seed points to the muscles, the skin, and other tissues in association with each other on the ultrasound synthesized image. The first seed point imparting module 354' may further impart seed points corresponding to the skin and other tissues to predetermined positions in the upper direction and the lower direction with respect to the reference point Pr.

The region demarcation module 355 is a functional block for demarcating a region to which each seed point imparted by the first seed point imparting module 354' and the second seed point imparting module 356 belongs. Since the mode for demarcating the region is the same as that in the first embodiment, the description is omitted.

The ultrasound stitched image divided into a plurality of regions by the region demarcation module 355 is output to the display interface module 36, and in response, the display interface module 36 displays the ultrasound stitched image on the display 31 in such a manner that the divided regions can be discriminated.

As described above, in the present embodiment, the reference point is set and the seed point is imparted in a manner different from the first embodiment. Specifically, instead of using the template image, the reference point setting module 353' sets the position with the largest luminance value on the line passing through the navel portion and extending in the transmission direction of the ultrasound wave as the reference point Pr. The first seed point imparting module 354' searches two pathways with the reference point Pr as a search starting point and a line crossing from the front side to the rear side of the rectus abdominis as a search end point by the Dijkstra method, and imparts a seed point to a region sandwiched between the searched two pathways. The second seed point imparting module 356 selects at least one ultrasound image from a plurality of ultrasound images for generating an ultrasound stitched image, imparts a seed point corresponding to the skin at a position on the ultrasound stitched image corresponding to any position on the upper end of the selected ultrasound image, and imparts a seed point corresponding to the tissue other than the skin and the muscle at a position on the ultrasound stitched image corresponding to any position on the lower end of the selected ultrasound image.

The present invention is not limited to the above embodiments, and various modifications can be made within the scope of the claims, and forms obtained by appropriately combining the technical means disclosed in each embodiment are also within the scope of the present invention.

For example, the mode described in the first embodiment may be adopted for setting the reference point, and the mode described in the second embodiment may be adopted for imparting the seed point. In addition, regarding the seed point impartment, seed points may be automatically assigned to some organizations (for example, muscle,), and seed points may be manually imparted to other organizations.

In the above embodiment, the case where the analyte is the abdomen has been described, but the present invention is not limited to the abdomen. Further, in the above embodiment, the ultrasound stitched image is divided into three types of muscles, skin, and other tissues, but the types of biological tissues for dividing the ultrasound stitched image are not limited thereto. For example, the type of biological tissue may include bone, hematoma, etc.

In the above embodiment, the ultrasound image generated by the image generation module 351 is an ultrasound stitched image obtained by stitching a plurality of ultrasound images, but may be a single ultrasound image. That is, the image generation module 351 may have only the ultrasound image generation module 3511.

While the present invention is applicable to both medical and non-medical applications, it is particularly suitable for applications in which a subject who is not a medical practitioner routinely confirms his or her health.

Terminology

It is to be understood that not necessarily all objects or advantages may be achieved in accordance with any particular embodiment described herein. Thus, for example, those skilled in the art will recognize that certain embodiments may be configured to operate in a manner that achieves or optimizes one advantage or group of advantages as taught herein without necessarily achieving other objects or advantages as may be taught or suggested herein.

All of the processes described herein may be embodied in, and fully automated via, software code modules executed by a computing system that includes one or more computers or processors. The code modules may be stored in any type of non-transitory computer-readable medium or other computer storage device. Some or all the methods may be embodied in specialized computer hardware.

Many other variations than those described herein will be apparent from this disclosure. For example, depending on the embodiment, certain acts, events, or functions of any of the algorithms described herein can be performed in a different sequence, can be added, merged, or left out altogether (e.g., not all described acts or events are necessary for the practice of the algorithms) Moreover, in certain embodiments, acts or events can be performed concurrently, e.g., through multi-threaded processing, interrupt processing, or multiple processors or processor cores or on other parallel architectures, rather than sequentially. In addition, different tasks or processes can be performed by different machines and/or computing systems that can function together.

The various illustrative logical blocks and modules described in connection with the embodiments disclosed herein can be implemented or performed by a machine, such as a processor. A processor can be a microprocessor, but in the alternative, the processor can be a controller, microcontroller, or state machine, combinations of the same, or the like. A processor can include electrical circuitry configured to process computer-executable instructions. In another embodiment, a processor includes an application specific integrated circuit (ASIC), a field programmable gate array (FPGA) or other programmable device that performs logic operations without processing computer-executable instructions. A processor can also be implemented as a combination of computing devices, e.g., a combination of a digital signal processor module (DSP) and a microprocessor, a plurality of microprocessors, one or more microprocessors in conjunction with a DSP core, or any other such configuration. Although described herein primarily with respect to digital technology, a processor may also include primarily analog components. For example, some or all of the signal processing algorithms described herein may be implemented in analog circuitry or mixed analog and digital circuitry. A computing environment can include any type of computer system, including, but not limited to, a computer system based on a microprocessor, a mainframe computer, a digital signal processor, a portable computing device, a device controller, or a computational engine within an appliance, to name a few.

Conditional language such as, among others, "can," "could," "might" or "may," unless specifically stated otherwise, are otherwise understood within the context as used in general to convey that certain embodiments include, while other embodiments do not include, certain features, elements and/or steps. Thus, such conditional language is not generally intended to imply that features, elements and/or steps are in any way required for one or more embodiments or that one or more embodiments necessarily include logic for deciding, with or without user input or prompting, whether these features, elements and/or steps are included or are to be performed in any particular embodiment.

Disjunctive language such as the phrase "at least one of X, Y, or Z," unless specifically stated otherwise, is otherwise understood with the context as used in general to present that an item, term, etc., may be either X, Y, or Z, or any combination thereof (e.g., X, Y, and/or Z). Thus, such disjunctive language is not generally intended to, and should not, imply that certain embodiments require at least one of X, at least one of Y, or at least one of Z to each be present.

Any process descriptions, elements or blocks in the flow diagrams described herein and/or depicted in the attached figures should be understood as potentially representing modules, segments, or portions of code which include one or more executable instructions for implementing specific logical functions or elements in the process. Alternate implementations are included within the scope of the embodiments described herein in which elements or functions may be deleted, executed out of order from that shown, or discussed, including substantially concurrently or in reverse order, depending on the functionality involved as would be understood by those skilled in the art.

Unless otherwise explicitly stated, articles such as "a" or "an" should generally be interpreted to include one or more described items. Accordingly, phrases such as "a device configured to" are intended to include one or more recited devices. Such one or more recited devices can also be collectively configured to carry out the stated recitations. For example, "a processor configured to carry out recitations A, B and C" can include a first processor configured to carry out recitation A working in conjunction with a second processor configured to carry out recitations B and C. The same holds true for the use of definite articles used to introduce embodiment recitations. In addition, even if a specific number of an introduced embodiment recitation is explicitly recited, those skilled in the art will recognize that such recitation should typically be interpreted to mean at least the recited number (e.g., the bare recitation of "two recitations," without other modifiers, typically means at least two recitations, or two or more recitations).

It will be understood by those within the art that, in general, terms used herein, are generally intended as "open" terms (e.g., the term "including" should be interpreted as "including but not limited to," the term "having" should be interpreted as "having at least," the term "includes" should be interpreted as "includes but is not limited to," etc.).

For expository purposes, the term "horizontal" as used herein is defined as a plane parallel to the plane or surface of the floor of the area in which the system being described is used or the method being described is performed, regardless of its orientation. The term "floor" can be interchanged with the term "ground" or "water surface." The term "vertical" refers to a direction perpendicular to the horizontal as just defined. Terms such as "above," "below," "bottom," "top," "side," "higher," "lower," "upper," "over," and "under," are defined with respect to the horizontal plane.

As used herein, the terms "attached," "connected," "mated" and other such relational terms should be construed, unless otherwise noted, to include removable, moveable, fixed, adjustable, and/or releasable connections or attachments. The connections/attachments can include direct connections and/or connections having intermediate structure between the two components discussed.

Numbers preceded by a term such as "approximately," "about," and "substantially" as used herein include the recited numbers, and also represent an amount close to the stated amount that still performs a desired function or achieves a desired result. For example, the terms "approximately," "about," and "substantially" may refer to an amount that is within less than 10% of the stated amount. Features of embodiments disclosed herein preceded by a term such as "approximately," "about," and "substantially" as used herein represent the feature with some variability that still performs a desired function or achieves a desired result for that feature.

It should be emphasized that many variations and modifications may be made to the above-described embodiments, the elements of which are to be understood as being among other acceptable examples. All such modifications and variations are intended to be included herein within the scope of this disclosure and protected by the following claims.

What is claimed is:

1. An ultrasound imaging device, comprising:
   processing circuitry configured
      to receive ultrasound waves transmitted from a surface of an analyte towards an inside of the analyte and reflected therein, and generate an ultrasound image of the inside of the analyte;
      to direct a portion of the analyte included in the ultrasound image in a predetermined direction by adjusting a rotation angle of the ultrasound image based on a line symmetrical region in the ultrasound image, where the line symmetrical region has a shape of line symmetry with respect to a digital line that is a central axis;
      to set a reference point in the rotation angle adjusted ultrasound image by matching a template image of the ultrasound image including the reference point while superimposing the template image on the ultrasound image, wherein, the reference point is included in a linea alba existing between a pair of right and left rectus abdominis muscles of an abdomen;
  to search first and second pathways between the reference point as a search start point and a line crossing from a front side to a rear side of the rectus abdominis muscle by a Dijkstra method, such that the first pathway is from the search start point to an end point at the front side and the second pathway is from the search start point to an end point at the rear side;
  to impart one or more muscle seed points to a muscle region between the first and second searched pathways as a muscle; and
  to demarcate a seed region to which a seed point belongs, and divide an image region of the analyte included in the ultrasound image into a plurality of regions according to a type of tissue.

2. The ultrasound imaging device of claim 1, wherein:
the processing circuitry imparts the seed point at a predetermined position relative to the reference point.

3. The ultrasound imaging device of claim 2, wherein:
the ultrasound image is an ultrasound stitched image of a cross section of the analyte, obtained by stitching a plurality of ultrasound images generated based on ultrasound waves transmitted from a plurality of mutually different positions on the surface of the analyte towards the inside of the analyte and reflected therein.

4. The ultrasound imaging device of claim 1, wherein:
the ultrasound image is an ultrasound stitched image of a cross section of the analyte, obtained by stitching a plurality of ultrasound images generated based on ultrasound waves transmitted from a plurality of mutually different positions on the surface of the analyte towards the inside of the analyte and reflected therein.

5. The ultrasound imaging device of claim 4, wherein the processing circuitry is further configured
  to select at least one ultrasound image from the plurality of ultrasound images for generating an ultrasound stitched image, and impart a skin seed point corresponding to the skin at a position on the ultrasound stitched image corresponding to a position on an upper end of the selected at least one ultrasound image.

6. The ultrasound imaging device of claim 5, wherein:
the processing circuitry imparts an other seed point to a position on the ultrasound stitched image corresponding to a position on a lower end of the selected at least one ultrasound image in association with the tissue other than skin and muscle.

7. The ultrasound imaging device of claim 1, wherein:
the processing circuitry directs a navel portion of the analyte included in the ultrasound image in the predetermined direction by adjusting a direction of the ultrasound image based on the line symmetrical regions in the ultrasound image.

8. The ultrasound imaging device of claim 7, wherein:
the processing circuitry sets, as the reference point, a position a luminance value equal to or higher than a predetermined threshold value, on a transmission direction line extending in the transmission direction of the ultrasound wave through the navel portion.

9. The ultrasound imaging device of claim 8, wherein:
the processing circuitry sets a position with the largest luminance value as the reference point on the line extending in the transmission direction of the ultrasound wave through the navel portion.

10. An ultrasound imaging method, comprising:
  receiving ultrasound waves transmitted from a surface of an analyte towards an inside of the analyte and reflected therein, and generating an ultrasound image of the inside of the analyte;
  directing a portion of the analyte included in the ultrasound image in a predetermined direction by adjusting a rotation angle of the ultrasound image based on a line symmetrical region in the ultrasound image, where the line symmetrical region has a shape of line symmetry with respect to a digital line that is a central axis;
  setting a reference point in the rotation angle adjusted ultrasound image by matching a template image of the ultrasound image including the reference point while superimposing the template image on the ultrasound image, wherein, the reference point is included in a linea alba existing between a pair of right and left rectus abdominis muscles of an abdomen;
  searching first and second pathways between the reference point as a search start point and a line crossing from a front side to a rear side of the rectus abdominis muscle by a Dijkstra method, such that the first pathway is from the search start point to an end point at the front side and the second pathway is from the search start point to an end point at the rear side;
  imparting one or more muscle seed points to a muscle region between the first and second searched pathways as a muscle; and
  demarcating a seed region to which a seed point belongs, and dividing an image region of the analyte included in the ultrasound image into a plurality of regions according to a type of tissue.

11. A non-transitory computer-readable recording medium storing a program causing a processor of an ultrasound imaging apparatus to execute processing, the processor configured to control operation of the ultrasound imaging apparatus, the processing comprising:
  receiving ultrasound waves transmitted from a surface of an analyte towards an inside of the analyte and reflected therein, and generating an ultrasound image of the inside of the analyte;
  directing a portion of the analyte included in the ultrasound image in a predetermined direction by adjusting a rotation angle of the ultrasound image based on a line symmetrical region in the ultrasound image, where the line symmetrical region has a shape of line symmetry with respect to a digital line that is a central axis;
  setting a reference point in the rotation angle adjusted ultrasound image by matching a template image of the ultrasound image including the reference point while superimposing the template image on the ultrasound image, wherein, the reference point is included in a linea alba existing between a pair of right and left rectus abdominis muscles of an abdomen;
  searching first and second pathways between the reference point as a search start point and a line crossing from a front side to a rear side of the rectus abdominis muscle by a Dijkstra method, such that the first pathway is from the search start point to an end point at the front side and the second pathway is from the search start point to an end point at the rear side;
  imparting one or more muscle seed points to a muscle region between the first and second searched pathways as a muscle; and demarcating a seed region to which a seed point belongs, and dividing an image region of the analyte included in the ultrasound image into a plurality of regions according to a type of tissue.

\* \* \* \* \*